(12) United States Patent
Adachi et al.

(10) Patent No.: US 8,187,843 B2
(45) Date of Patent: May 29, 2012

(54) METHOD FOR PRODUCTION OF L-GLUTAMINE

(75) Inventors: Yugo Adachi, Hofu (JP); Mikiro Hayashi, Tsukuba (JP); Akihiro Senoo, Tsukuba (JP); Yoshiyuki Yonetani, Tsukuba (JP); Shin-ichi Hashimoto, Hofu (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 304 days.

(21) Appl. No.: 12/439,300

(22) PCT Filed: Aug. 30, 2007

(86) PCT No.: PCT/JP2007/066910
§ 371 (c)(1),
(2), (4) Date: May 4, 2009

(87) PCT Pub. No.: WO2008/026698
PCT Pub. Date: Mar. 6, 2008

(65) Prior Publication Data
US 2011/0124059 A1 May 26, 2011

(30) Foreign Application Priority Data
Sep. 1, 2006 (JP) ................................. 2006-237332

(51) Int. Cl.
*C12P 13/14* (2006.01)
(52) U.S. Cl. ....................................................... 435/110
(58) Field of Classification Search .................... 435/110
See application file for complete search history.

(56) References Cited

FOREIGN PATENT DOCUMENTS

| EP | 1 038 970 A2 | 9/2000 |
| JP | 2000-270872 A | 10/2000 |
| WO | 0014241 | * 3/2000 |

OTHER PUBLICATIONS

Kronemeyer et al., *Journal of Bacteriology*, 177: 1152-1158 (Mar. 1995).
Niebisch et al., *The Journal of Biological Chemistry*, 281(18): 12300-12307 (May 5, 2006).
Database Geneseq [Online], Database Accession No. AAG92769 (Sep. 26, 2001, revised Jun. 15, 2007).
Database Geneseq [Online], Database Accession No. AAG93220 (Sep. 26, 2001, revised Jun. 15, 2007).
Database Geneseq [Online], Database Accession No. ADD13443 (Jan. 1, 2004, revised Jun. 15, 2007).
Database Geneseq [Online], Database Accession No. ADD13667 (Jan. 1, 2004, revised Jun. 14, 2007).
Kalinowski et al., *Journal of Biotechnology*, 104(1-03): 5-25 (2003).
European Patent Office, Supplementary European Search Report in European Application No. 07 80 6387 (Jul. 29, 2011).

* cited by examiner

*Primary Examiner* — Tekchand Saidha
(74) *Attorney, Agent, or Firm* — Leydig, Voit & Mayer, Ltd.

(57) ABSTRACT

According to the present invention, it is possible to provide a microorganism belonging to the genus *Corynebacterium*, wherein the activity of (1) a protein having the amino acid sequence shown by any one of SEQ ID NO:1 to 3, or (2) a protein having a homology of 80% or more to the amino acid sequence shown by any one of SEQ ID NO:1 to 3, and having substantially the same activity as the activity of a protein having the amino acid sequence shown by any one of SEQ ID NO:1 to 3, has been reduced or lost, and wherein the activity of (3) a protein having the amino acid sequence shown by SEQ ID NO:4, or (4) a protein having a homology of 80% or more to the amino acid sequence shown by SEQ ID NO:4, and having substantially the same activity as the activity of a protein having the amino acid sequence shown by SEQ ID NO:4, has been reduced or lost, and a process for producing L-glutamine using the microorganism and the like.

4 Claims, No Drawings

SEQUENCE LISTING

```
<160> NUMBER OF SEQ ID NOS: 42

<210> SEQ ID NO 1
<211> LENGTH: 462
<212> TYPE: PRT
<213> ORGANISM: Corynebacterium glutamicum ATCC13032

<400> SEQUENCE: 1

Met Asp Thr Asp Asp Ser Pro Asp His Trp Leu Asp Pro Leu Thr Glu
1               5                   10                  15

Lys Asp Thr Ser Lys Arg Thr Leu Val Asn Ser Ile Val Gln Glu Thr
                20                  25                  30

Phe Gly Gln Pro Ile Phe Val Ala Arg Lys Ile Trp Ala Phe Val Asn
            35                  40                  45

Thr Ser Pro Gly Arg Met Thr Leu Met Thr Ile Ile Ile Ser Ile Ala
        50                  55                  60

Ile Phe Ala Ala Gly Tyr Ala Met Ser Val Ser Ser Asp Thr Arg Gln
65                  70                  75                  80

Ser Asn Leu Asp Asp Leu Ile Thr Asn Ala Glu Pro Val Ser Tyr Asn
                85                  90                  95

Ala His Val Leu Tyr Thr Ser Leu Ser Val Ala Asp Thr Thr Ala Thr
            100                 105                 110

Thr Gly Phe Val Gln Ala Gly Val Glu Gly Pro Val Asn Arg Val Lys
        115                 120                 125

Tyr His Thr Ala Ile Asp Arg Ala Ala Val Ala Ala Thr His Thr Ala
130                 135                 140

Ala Ser Ala Asp Ser Ser Asn Glu His Leu Met Glu Leu Val Leu Glu
145                 150                 155                 160

Ile Gln Arg Gln Leu Pro Val Tyr Thr Gly Leu Val Glu Thr Ala Arg
                165                 170                 175

Thr Asn Asn Arg Ala Gly Asn Pro Val Gly Val Ala Tyr Met Ser Glu
            180                 185                 190

Ala Ser Ala Met Met Arg Asn Glu Ile Leu Pro Met Ala Ser Glu Leu
        195                 200                 205

Tyr Asn Leu Thr Ser Arg Ala Val Ser Asp Gln Gln Arg Ser Val Thr
210                 215                 220
```

```
Gly Pro Gln Trp Phe Pro Leu Ser Gly Leu Leu Ala Ala Leu Ala Met
225                 230                 235                 240

Leu Ile Val Ala Gln Trp Trp Leu Met Arg Ile Thr Arg Arg Arg Ile
            245                 250                 255

Asn Lys Gly Phe Ala Leu Ala Thr Val Met Met Thr Ala Thr Leu
                260                 265                 270

Trp Val Ser Ala Ala Asn Trp Ala Thr Trp Gln Ala Gly Thr Lys Gly
            275                 280                 285

Phe Glu Glu Ala Ser Gly Pro Leu Asn Ser Met Thr Thr Ala Arg Ile
290                 295                 300

Tyr Ala Gln Gln Thr Arg Thr Thr Glu Thr Leu Ser Leu Val Arg Arg
305                 310                 315                 320

Gln Ser Ile Gln Gly Ser Gly Thr Gly Phe Thr Ala Thr Ile Asn Gln
                325                 330                 335

Ile Lys Arg Ala Leu Asp Glu Tyr Gly Thr Thr Ala Gln Ser Gln Thr
                340                 345                 350

Pro Glu His Gln Gln Leu Ile Thr Ala Ile Arg Asn Ala Ile Ala Ala
                355                 360                 365

Trp Thr Ala Asp His Asp Glu Phe Thr Val Leu Leu Ala Ser Gly Asp
    370                 375                 380

Tyr Asn Gly Ala Val Asn Ala Val Leu Asn Lys Asp Glu Glu Gly Gln
385                 390                 395                 400

Thr Ser Phe Asp Glu Leu Asp Thr Ala Leu Ala Glu Leu Ile Ala Asp
                405                 410                 415

Ser Arg Ser Ser Met Arg Ser Tyr Ile Gln Ser Gly Leu Gln Ala Thr
                420                 425                 430

Glu Leu Val Ser Val Met Val Met Ile Leu Ser Val Val Ser Val Leu
                435                 440                 445

Ala Leu Trp Val Gly Ile Arg Pro Arg Leu Gln Glu Tyr Leu
    450                 455                 460

<210> SEQ ID NO 2
<211> LENGTH: 344
<212> TYPE: PRT
<213> ORGANISM: Corynebacterium glutamicum ATCC13032

<400> SEQUENCE: 2

Met His Ala Phe Arg Arg Pro Pro Leu Thr Thr Arg Val Gly Ala
1               5                   10                  15

Ala Leu Leu Ala Ala Thr Leu Leu Ala Ser Cys Thr Pro Thr Pro Val
            20                  25                  30

Glu Pro Ala Glu Thr Leu Thr Ala Leu Asp Pro Asp Ala Gly Pro Pro
                35                  40                  45

Leu Pro Pro Asp Ser Ser Ile Glu Ala Pro Gly Glu Lys Glu Pro Ile
    50                  55                  60

Val Glu Val Ile Glu Asn Trp Pro Gly Ser Leu Arg Pro Asp Asp Leu
65                  70                  75                  80

Thr Pro Glu Glu Arg Val Pro Gly Ile Val Asn Arg Gly Arg Ile Ile
                85                  90                  95

Val Gly Val Asp Gln Ser Gln Asn Leu Leu Ser Phe Arg Asp Pro Val
                100                 105                 110

Thr Gly Glu Leu Arg Gly Phe Glu Val Glu Leu Ala Arg Glu Ile Ser
            115                 120                 125

Arg Asp Ile Phe Gly Asp Pro Asn Lys Val Asp Phe Arg Phe Val Gly
    130                 135                 140
```

```
Ser Ser Asp Arg Leu Arg Ser Leu Asp Gln Gly Val Asp Ile Val
145                 150                 155                 160

Ile Arg Ser Val Thr Ile Asp Glu Arg Ala Lys Leu Val Glu Phe
                165                 170                 175

Ser Thr Pro Tyr Leu Arg Thr Gln Thr Arg Met Leu Thr Met Glu Ser
            180                 185                 190

Ser Gly Ile Thr Ser Ile Ala Asp Leu Pro Gly His Thr Ile Cys Val
            195                 200                 205

Thr Asp Gly Ser Thr Ser Leu Gln Arg Ala Arg Thr Ile Ala Pro Glu
210                 215                 220

Ala Ser Ile Leu Lys Thr Arg Asn Trp Ser Asp Cys Leu Met Ala Leu
225                 230                 235                 240

Gln Gln His Gln Ala Gln Val Ile Leu Gly Asp Val Ile Leu Ser
                245                 250                 255

Gly Ile Ala Ala Gln Asp Pro Tyr Thr Glu Ile Leu Asp Thr Ser Leu
            260                 265                 270

Asp Ser His Ser Tyr Gly Val Ala Ala Ser Thr Thr Ala Glu Thr
                275                 280                 285

Asp Ser Ser Gly Leu Ile Arg Gln Val Asn Tyr Thr Ile Glu Arg Ile
290                 295                 300

Arg Thr Asp Arg Met Trp Trp Thr Met Phe Asp Asp Trp Phe Gly Pro
305                 310                 315                 320

Tyr Leu Trp Ser Tyr Gly Pro Pro Gln Leu Gln Tyr Met Pro Glu Glu
                325                 330                 335

Glu Gly Thr Glu Asn Asp Glu Gly
            340

<210> SEQ ID NO 3
<211> LENGTH: 822
<212> TYPE: PRT
<213> ORGANISM: Corynebacterium glutamicum ATCC13032

<400> SEQUENCE: 3

Met Lys Asp Asn Glu Asp Phe Asp Pro Asp Ser Pro Ala Thr Glu Ala
1               5                   10                  15

Val Ala Phe Asn Pro Phe Asp Asp Asp Glu Asp Asp Ser Pro Ala
                20                  25                  30

Thr Ser Ala Val Ala Phe Asn Pro Phe Glu Asp Asp Asp Asp Asp
            35                  40                  45

Glu Phe Gln Gly Glu Gly Leu Glu Phe Leu Leu Arg Asp Leu Asp Asn
50                  55                  60

Leu Arg Ala Thr Gln Gly Gln Met Val Val Glu Gln Pro Ala Val Glu
65                  70                  75                  80

Asp Ser Leu Gly Ser Ala Ser Ala His Thr Glu Thr Ala Ala Ser
                85                  90                  95

Leu Arg Pro Arg Pro Glu Val Asp Pro Ser Gly Arg Ser Arg Arg Gln
            100                 105                 110

Ala Ile Ser Leu Phe Arg Glu Arg Arg Val Arg Arg Gln Ser Arg
            115                 120                 125

Pro Val Ala Asp Gly Met Val Glu Leu Pro Phe Ile Thr Pro Lys Pro
            130                 135                 140

Glu Asp Glu Leu Leu Ile Asp Pro Glu Lys Lys Arg Lys Pro Gly Val
145                 150                 155                 160

Ala Ala Pro Gln Leu Val Ala Gly Asp Ile Val Ala Glu Gln Tyr Glu
                165                 170                 175
```

-continued

```
Val Leu Gly Val Ile Ala His Gly Gly Met Gly Trp Ile Tyr Leu Ala
            180                 185                 190
Asn Asp Arg Asn Val Ser Gly Arg Ile Val Leu Lys Gly Met Met
            195                 200                 205
Ala Gln Ser Ser Val Gln Asp Gln Gly Thr Ala Glu Ala Arg Glu
    210                 215                 220
Phe Leu Ala Asp Ile Thr His Pro Gly Ile Val Lys Ala Tyr Asn Phe
225                 230                 235                 240
Ile Asp Asp Pro Arg Val Pro Gly Gly Phe Ile Val Met Glu Tyr Val
                245                 250                 255
Asn Gly Pro Ser Leu Lys Asp Arg Cys Lys Ala Gln Pro Asp Gly Val
            260                 265                 270
Leu Arg Val Asp Leu Ala Ile Gly Tyr Ile Leu Glu Leu Leu Pro Ala
        275                 280                 285
Met Asp Tyr Leu His Gln Arg Gly Val Val Tyr Asn Asp Leu Lys Pro
    290                 295                 300
Glu Asn Val Ile Ala Thr Glu Asp Gln Val Lys Leu Ile Asp Leu Gly
305                 310                 315                 320
Ala Val Thr Gly Ile Gly Ala Phe Gly Tyr Ile Tyr Gly Thr Lys Gly
                325                 330                 335
Phe Gln Ala Pro Glu Val Ala Thr His Gly Pro Ser Ile Ser Ser Asp
            340                 345                 350
Ile Phe Thr Ile Gly Arg Thr Leu Ala Ala Leu Thr Met Pro Leu Pro
        355                 360                 365
Val Glu Asp Gly Val Leu Ala Pro Gly Ile Pro Ser Pro Lys Asn Ser
    370                 375                 380
Pro Leu Leu Arg Arg His Leu Ser Phe Tyr Arg Leu Leu Gln Arg Ala
385                 390                 395                 400
Thr Ala Asp Asp Pro Gln His Arg Phe Arg Asn Val Ser Glu Leu Arg
                405                 410                 415
Thr Gln Leu Tyr Gly Val Leu Arg Glu Ile Leu Ala Val Arg Asp Gly
            420                 425                 430
Lys Gln Tyr Pro Pro Gln His Ser Leu Phe Ser Pro Gln Arg Ser Thr
        435                 440                 445
Phe Gly Thr Lys His Leu Val Phe Arg Thr Asp Arg Ile Ile Asp Gly
    450                 455                 460
Ile Glu Arg Gln Ala Arg Ile Thr Ala Pro Glu Ile Val Ser Ala Leu
465                 470                 475                 480
Pro Val Pro Leu Ile Asp Arg Thr Asp Pro Gly Ala Arg Met Leu Ser
                485                 490                 495
Gly Ser Ser Tyr Ala Glu Pro Ser Glu Thr Leu Glu Thr Leu Arg Asn
            500                 505                 510
Ser Met Glu Asp Glu Gln Tyr Arg Gln Ser Ile Glu Ile Pro Leu Gly
        515                 520                 525
Val Val Arg Ala Leu Leu Asp Leu Gly Phe Thr Thr Glu Ala Arg Gln
    530                 535                 540
Trp Leu Glu Thr Leu Glu Gly Arg Ile Gly Asp Asp Trp Arg His Lys
545                 550                 555                 560
Trp Phe Ser Gly Ile Thr Tyr Leu Leu Leu Asp Asp Tyr Ala Thr Ala
                565                 570                 575
Gln Val Phe Phe Asn His Val Leu Thr Ile Leu Pro Gly Glu Ala Ala
            580                 585                 590
Pro Lys Leu Ala Leu Ala Ala Val Asp Glu Leu Ile Leu Gln Gln Ile
        595                 600                 605
```

-continued

Gly Ala Glu Ser Thr Ala Tyr Leu Thr Pro Asp Ile Val Ser Ala Thr
610                 615                 620

Ala Thr Leu Ser Lys Asp Phe Glu Asp Leu Asp Ala Ser Ala Phe Glu
625                 630                 635                 640

Ser Leu Ser Asp Thr Trp Ser His Ile Ser Ser Asp Pro His Val Val
            645                 650                 655

Arg Phe His Ser Leu Arg Leu Tyr Ala Leu Val Trp Ala Thr Asn Pro
        660                 665                 670

Thr Thr Val Ser Ser Ala Phe Gly Leu Ala Arg Gln Leu Met Ala Glu
    675                 680                 685

Asn Gln Ile Glu Leu Ala Val Gln Ala Leu Asp Lys Leu Pro Gln Ser
690                 695                 700

Ser Thr His Tyr Arg Met Ala Thr Leu Thr Thr Ile Leu Leu Leu Val
705                 710                 715                 720

Ser Ser Asn Leu Ser Glu Ser Arg Ile Arg Arg Ala Ala Arg Arg Leu
            725                 730                 735

Thr Glu Ile Pro Thr Asn Glu Pro Arg Phe Asn Gln Ile Lys Ile Ala
        740                 745                 750

Ile Met Ser Ala Gly Leu Ser Trp Leu Arg Glu Arg Lys Leu Lys Ala
    755                 760                 765

Ser Ala Ser Ala Asn Pro Leu Phe Glu Tyr Pro Phe Ser Gln Lys Gly
770                 775                 780

Leu Arg Thr Gly Ile Ser Glu Ala Leu Arg Ile Gln Ala Arg Ser Ala
785                 790                 795                 800

Pro Phe Pro His His Arg Tyr Ala Leu Val Asp Met Ala Asn Ala Val
            805                 810                 815

Arg Pro Leu Ser Trp Phe
        820

<210> SEQ ID NO 4
<211> LENGTH: 295
<212> TYPE: PRT
<213> ORGANISM: Corynebacterium glutamicum ATCC13032

<400> SEQUENCE: 4

Met Ser Ala Lys Arg Thr Phe Thr Arg Ile Gly Ala Ile Leu Gly Ala
1               5                   10                  15

Thr Ala Leu Ala Gly Val Thr Leu Thr Ala Cys Gly Asp Ser Ser Gly
            20                  25                  30

Gly Asp Gly Phe Leu Ala Ala Ile Glu Asn Gly Ser Val Asn Val Gly
        35                  40                  45

Thr Lys Tyr Asp Gln Pro Gly Leu Gly Leu Arg Asn Pro Asp Asn Ser
    50                  55                  60

Met Ser Gly Leu Asp Val Asp Val Ala Glu Tyr Val Val Asn Ser Ile
65                  70                  75                  80

Ala Asp Asp Lys Gly Trp Asp His Pro Thr Ile Glu Trp Arg Glu Ser
                85                  90                  95

Pro Ser Ala Gln Arg Glu Thr Leu Ile Gln Asn Gly Glu Val Asp Met
            100                 105                 110

Ile Ala Ala Thr Tyr Ser Ile Asn Ala Gly Arg Ser Glu Ser Val Asn
        115                 120                 125

Phe Gly Gly Pro Tyr Leu Leu Thr His Gln Ala Leu Leu Val Arg Gln
    130                 135                 140

Asp Asp Asp Arg Ile Glu Thr Leu Glu Asp Leu Asp Asn Gly Leu Ile
145                 150                 155                 160

```
Leu Cys Ser Val Ser Gly Ser Thr Pro Ala Gln Lys Val Lys Asp Val
            165                 170                 175
Leu Pro Gly Val Gln Leu Gln Glu Tyr Asp Thr Tyr Ser Ser Cys Val
        180                 185                 190
Glu Ala Leu Ser Gln Gly Asn Val Asp Ala Leu Thr Thr Asp Ala Thr
            195                 200                 205
Ile Leu Phe Gly Tyr Ser Gln Gln Tyr Glu Gly Asp Phe Arg Val Val
        210                 215                 220
Glu Met Glu Lys Asp Gly Glu Pro Phe Thr Asp Glu Tyr Tyr Gly Ile
225                 230                 235                 240
Gly Leu Lys Lys Asp Asp Gln Glu Gly Thr Asp Ala Ile Asn Ala Ala
            245                 250                 255
Leu Glu Arg Met Tyr Ala Asp Gly Thr Phe Gln Arg Leu Leu Thr Glu
        260                 265                 270
Asn Leu Gly Glu Asp Ser Val Val Val Glu Glu Gly Thr Pro Gly Asp
            275                 280                 285
Leu Ser Phe Leu Asp Ala Ser
        290                 295

<210> SEQ ID NO 5
<211> LENGTH: 6882
<212> TYPE: DNA
<213> ORGANISM: Corynebacterium glutamicum ATCC13032
<220> FEATURE:
<221> NAME/KEY: CDS
<222> LOCATION: (1001)..(2389)
<220> FEATURE:
<221> NAME/KEY: CDS
<222> LOCATION: (2390)..(3424)
<220> FEATURE:
<221> NAME/KEY: CDS
<222> LOCATION: (3414)..(5882)

<400> SEQUENCE: 5
aggtggtttt ctgctgttct atttgggtgt gttgctttgg catcaagcag tgctcccact      60
ttggtcaggg gattttttgag cgatcggtag ggttgtcctt cgatcgtggc atgccctgca     120
gttggattat ctaagccaag gatcagccgc atcgtggtgg atttttccggc gccgttgggg    180
ccgagaaatc cggtgactat tccgggtttt acttcgaagc tcagatcatc gactgcgcgg     240
acctgaccat attgtttggt gaggccttca acgttgatca tgcgcaccag tgtcgcataa     300
acctactctg ttgtgttcag tagctttctt aaagagggcc acgctttggc gaatgctggc     360
atcaaagcca aagagtcaac cgctgcgata tctacccacc gtagttcgag ggattcttca     420
ttagcggtgg tatctagggt ttcgccggtt ttagttcgtg cgatgaccgt ggtgtaggtc     480
cagttgccgg caagttctgg gcgttctgga tcggcgggaa aagggcctgc ggtgactatt     540
gaatctaaaa cttccacgtc gtcgggcagg attccagttt cttcaaatgc ttcacgcagg     600
gctgattccg ctgcggtttc atgtgagtct cgtgcgcctc cagggagtgc ccaggtgtcg     660
ccgttgttgg tccatgcggc tcggtgctgc atgagcattt gtttatctgc taccaacaac     720
aatcctgctg ctccgttttt gccccatact gccccgccat gggtgctgc tgcccatcca     780
tcgccgtcgc ctttcatggt gtccacatta ggctaaacgc tggggtatt catcaaggta     840
gccaatactt tcaacatgtc atgagtcacg ctattctgaa acaatgatcc gggatggaaa     900
tggggagcat tcagaggtgc ctaatcctct ggatgattct gcggtgcaaa attcagcccc    960
acattcagcc ccacattcag ctcggacccg gttggagttt ttggataccg atgactcgcc   1020
tgatcattgg cttgatccgt taacggagaa ggatacttct aagcgcactc tcgttaattc   1080
```

```
gattgttcag gaaactttcg gccagcctat ttttgttgcc cgcaagattt gggctttcgt    1140
caatacgtcg ccgggccgga tgacgttgat gacgattatc atttcgatcg ccattttgc    1200 tgctggttac gccatgtcgg tgtcttcgga tactaggcag tccaatttgg atgatttgat    1260
cactaatgcg gagcctgttt cctataacgc gcatgtgctg tatacatcat tgtcggttgc    1320
tgataccact gctaccactg gttttgttca ggctggtgtg gagggcccgg tgaatcgggt    1380
gaagtatcac actgctattg atcgtgctgc ggttgctgct actcatactg cggcgtctgc    1440
ggatagtagt aatgagcatt tgatggagtt ggtgctggag attcagcgtc agttgccggt    1500
gtatacgggg ttggtggaaa ctgctcggac taataaccgt gcgggtaatc ccgtgggtgt    1560
ggcctatatg tctgaggcca gcgcgatgat gcgtaatgaa attttgccga tggcgtctga    1620
gctttacaac ctgacgagtc gtgcggtgtc tgatcagcag cgttcggtga cgggtccgca    1680
gtggtttccg ctgtctggat tgcttgcggc tcttgccatg ttgattgttg cgcagtggtg    1740
gttgatgcgg attacgcgca ggcgcatcaa caagggtttt gccctggcca cggtgatgat    1800
gatgacggca acgttatggg tgtcagctgc aaactgggcg acgtggcagg ctggcacgaa    1860
gggttttgag gaagcgtcgg ggccgttgaa ttccatgact acggctcgta tttatgcgca    1920
gcagacccgc acgacggaga cgttgtcgtt ggtgcgtagg cagtcgattc agggcagtgg    1980
cactggtttt accgcaacga ttaatcagat taagcgtgcg ctggatgagt atgaaaccac    2040
tgcgcagtca cagactccgg agcatcagca gttgattacg gcgattcgta atgcgattgc    2100
tgcatggact gccgatcacg atgagttcac ggtgttgttg gcgtctggtg attacaacgg    2160
tgcggtcaat gcggtgctca acaaagatga ggagggccag accagctttg atgagctcga    2220
tactgcgctg gctgagctga tcgcggattc tcgcagctcc atgcgttcct atatccagtc    2280
gggcctgcag gccacggagt tggtgtccgt catggtgatg attctgtctg tcgtttctgt    2340
gttggctttg tgggtcggca tccgcccccg tttgcaggag tacttataaa tgcacgcttt    2400
tcgacgcccc cctccactca ccacgcgagt cggcgctgca ttgctggccg caacgctgct    2460
tgcttcctgc actccaacac ctgtggaacc ggcagaaacc ttgactgctt tggatcccga    2520
tgccggtcca ccactgccac cggattcttc gattgaagct cccggtgaaa aagagcccat    2580
tgtggaagta atagagaatt ggccaggttc tttacgcccg gatgatctga cccctgagga    2640
gcgggtacct ggcatcgtca accgggggtcg catcattgtg ggtgtggatc aatcgcaaaa    2700
cttgctcagt ttccgtgatc cggtgactgg tgagctgcgc ggttttgaag tggaattagc    2760
gagggaaatt tcccgcgaca ttttcggtga ccccaataag gtggattttcc gattcgtcgg    2820 ctcgtccgac cgtctgcgtt cccttgacca aggtgatgta gatattgtga ttcgttccgt    2880
cacgatcacc gacgaacgcg ccaaattggt ggaattttcc acaccgtacc tgcgcaccca    2940
aacccgcatg ttgaccatgg aatcttcagg aatcacgtcc atcgcagatc tacccggcca    3000
caccatttgt gtcaccgatg gctccacttc attgcagcga gcccgcacca ttgcgccgga    3060
ggcctcaatc ttaaaaactc gcaattggtc cgattgtctc atggcgttgc agcagcatca    3120
ggctcaggtc attttgggcg atgatgtcat tttgtccggc atcgcagcac aggatcccta    3180
caccgagatt cttgataccct ccctcgattc ccattcctat ggagtggcag cggcatcgac    3240
cactgctgaa acagactctt cggggttgat tcggcaggta aactacacaa ttgaacggat    3300
ccgcacagac cgcatgtggt ggacaatgtt cgacgattgg tcggaccctt atctctggtc    3360
ctacggtcca ccacagctgc agtacatgcc agaggaagaa gggacagaaa cgatgaaggg    3420
ataatgaaga tttcgatcca gattcaccag caaccgaagc tgttgccttc aacccttttcg    3480
```

```
acgatgacga tgaggatgat tcccccgcta cctcagccgt tgcctttaac ccttttgaag    3540
atgacgatga cgacgatgag ttccaaggcg aaggcctaga attcctgctg cgcgacctcg    3600
acaatctgcg agccacccaa ggtcaaatgg tggtggaaca accagcagtt gaagacagcc    3660
tcgggtcagc atctgcgcat acggagacaa ctgcggcctc actgcgtccc cgcccagagg    3720
tggatccaag tgagaggagt cgtcgacaag caatttcgct gttccgcgaa cggcgccgcg    3780
taaggcgcca atcccgccca gttgctgatg gcatggtgga attgccgttc atcaccccca    3840
aaccggaaga tgagctgctc atcgacccgg aaaagaagcg caaacctggt gtggcagcgc    3900
cgcaacttgt cgcgggcgat atcgtcgcag agcaatatga agtcctcggc gtcatcgcgc    3960
acggcggcat gggttggatt tacctcgcca acgaccgcaa tgtgtccggc cgcatcgtgg    4020
tgctcaaagg catgatggcg caatcttccg ttcaagacca aggcaccgct gaagccgaac    4080
gcgaattcct cgccgacatc acccaccccg gcatcgtgaa ggcctacaac ttcatcgacg    4140
accccgcgt cccggcgga ttcatcgtca tggaatacgt caacggcccc tccctgaaag     4200
accgctgcaa agcccaaccc gacggcgtgc tccgcgtcga cctcgccatc ggctacatcc    4260
tcgaactcct ccccgccatg gactacctgc accaacgcgg cgtagtgtac aacgacctca    4320
aacccgaaaa cgtcatcgcc accgaagacc aagttaaact catcgacctc ggcgcggtta    4380
ccggcatcgg cgcattcggc tacatttacg gcaccaaagg attccaagca cccgaagtag    4440
ccacccatgg cccctcaatc tcctccgata ttttcaccat cggacgcacc ctcgcagcac    4500
tcaccatgcc cctccccgtt gaagacggtg tcctcgcacc gggcatcccc tcgcccaaaa    4560
attcacctct tctgcgcagg catttgtcgt tctaccgcct cctgcaacgc gccaccgccg    4620
acgaccccca acaccgattc cgcaacgtca gcgaactacg cacccaactc tacgcgtac    4680
tgcgtgaaat tttggcagtc cgcgacggca acaatacccg ccacagcac tcactattct     4740
ccccacagcg aagcaccttt ggcaccaaac acctcgtgtt ccgcaccgac cgcatcatcg    4800
acggcatcga acgacaagca cgcatcacag caccagaaat tgtctccgcg ctgcctgtcc    4860
cactcatcga ccgcaccgac cccggcgccc gtatgctctc cggatcctcc tatgcagaac    4920
cctccgaaac cctggaaact ctgcgcaact ccatggaaga cgagcaatac cgccaatcaa    4980
tcgagatccc cctcggtgtc gtccgagccc tccttgacct aggctttacc accgaagcac    5040
gccaatggct cgaaacccta gagggacgca tcggcgacga ctggcgacac aaatggttct    5100
ccggaatcac ctacctcctc ctcgacgact acgccaccgc ccaagtattc ttcaaccacg    5160
tcctgaccat cctgcccggc gaagccgctc ctaaactagc cctcgcagct gttgacgaac    5220
tcatcctcca acaaatcggc gccgaatcca ccgcctatct caccccagac atcgtctctg    5280
caaccgcgac cctcagcaaa gatttcgaag acctcgacgc ctccgccttc gaatcactca    5340
gcgacacctg gtcccacatc tccagcgacc cacacgtagt ccgcttccat tcactgcgcc    5400
tctacgcact tgtctgggca accaaccca ccaccgtgtc ctccgcgttc gggctcgccc     5460
gccaactcat ggccgaaaac caaatcgaac tcgcagtcca agccctagac aaaactcccc    5520
aatcatccac ccactaccga atggccaccc tcaccaccat cttgttgctg gtcagctcca    5580
atttgagtga atcccgcatc cgacgggctg ccgccgact caccgaaatc cccacaaacg     5640
aaccccgctt caaccaaatc aaaattgcca tcatgtcggc aggcctcagc tggcttcgag    5700
agcgaaaact caaagcttcc gcctccgcga acctttgtt tgaatacccg ttctcccaaa     5760
aaggcctgcg caccggcatc tccgaggcac tccgcattca ggcacgttct gcaccgttcc    5820
cgcaccaccg ttacgcactt gtggatatgg cgaatgccgt gcggccactg agttggttct    5880
```

```
agctgttttg acttgggget atttggtagg tggcgattta agggccttta ggagtgcgat    5940
gtccccTagt ttgactttgg gcgagttagg cccttagaag cgattctggg ggagttactt    6000
ttgggacaat tggggctgat gtgatttctg cggggttact gcaggtttcc tgttcaactt    6060
ctcgttacgg gttgctggaa ttcgatgaaa tggaacgaat attcgcataa tagcaaggtg    6120
ttagagcaaa ttttcgacca aaaccggcct tttaatgttc ggtggggacg aaaattcgca    6180
accccaagag gtctagggc caacaagcga ttcctgtgaa gctccagggc aaggatccac     6240
cacgttccaa aggaaaactg ggatctgtgg tggatccgtg cagtttcacc ccttaaaaac    6300
gcaaaaatcc accacaaaac cgctgatcag agcgatttgt ggtggatcct aaccaggaga    6360
gctaagcgaa cttcaccgcg tacctagcga tagctaactc ttcattagtt ggaataacaa    6420
acaccttcac cttggaggca tcggtggaaa tcaatcgagg accatcgttt ggcaatgcgt    6480
tacgctctgg atcgatctca attccgtaca tttccaaacc tgccaaggca tcctcacgga    6540
caaactgggc attttcaccg acaccggcgg tgaaacgat ggtgtctacc cgtcccagtg      6600
ccaccatgta ggaaccgagg tagcggcgga gttggtgtat gtaaatgttg tacgcggacc    6660
aggcatcttg atcattgttg tcgatcattt cccgcagttc acggaaatca ttaacaccgg    6720 aaagtcccctt tacacccgac ttttttgttca gcagattatc gatctcatcg atgctcatgc   6780
cagcggtgcg ggaaaggtgg aagacgatac ctggatcaat gtcaccgctt cgggtaccca    6840
tgacaaggcc cgcgagaggt gtcataccca tggaagtatc ta                       6882
```

<210> SEQ ID NO 6
<211> LENGTH: 20
<212> TYPE: DNA
<213> ORGANISM: Artificial Sequence
<220> FEATURE:
<223> OTHER INFORMATION: Synthetic DNA

<400> SEQUENCE: 6
gaggccttca acgttgatca                                                  20

<210> SEQ ID NO 7
<211> LENGTH: 40
<212> TYPE: DNA
<213> ORGANISM: Artificial Sequence
<220> FEATURE:
<223> OTHER INFORMATION: Synthetic DNA

<400> SEQUENCE: 7
gggcgtcgaa aagcgtgcat aaactccaac cgggtccgag                            40

<210> SEQ ID NO 8
<211> LENGTH: 40
<212> TYPE: DNA
<213> ORGANISM: Artificial Sequence
<220> FEATURE:
<223> OTHER INFORMATION: Synthetic DNA

<400> SEQUENCE: 8
ctcggacccg gttggagttt atgcacgctt ttcgacgccc                            40

<210> SEQ ID NO 9
<211> LENGTH: 20
<212> TYPE: DNA
<213> ORGANISM: Artificial Sequence
<220> FEATURE:
<223> OTHER INFORMATION: Synthetic DNA

<400> SEQUENCE: 9
gcatgtactg cagctgtggt      20

<210> SEQ ID NO 10
<211> LENGTH: 20
<212> TYPE: DNA
<213> ORGANISM: Artificial Sequence
<220> FEATURE:
<223> OTHER INFORMATION: Synthetic DNA

<400> SEQUENCE: 10
cactgctatt gatcgtgctg      20

<210> SEQ ID NO 11
<211> LENGTH: 40
<212> TYPE: DNA
<213> ORGANISM: Artificial Sequence
<220> FEATURE:
<223> OTHER INFORMATION: Synthetic DNA

<400> SEQUENCE: 11
aatctggatc gaaatcttca ttataagtac tcctgcaaac      40

<210> SEQ ID NO 12
<211> LENGTH: 40
<212> TYPE: DNA
<213> ORGANISM: Artificial Sequence
<220> FEATURE:
<223> OTHER INFORMATION: Synthetic DNA

<400> SEQUENCE: 12
gtttgcagga gtacttataa tgaagatttc gatccagatt      40

<210> SEQ ID NO 13
<211> LENGTH: 20
<212> TYPE: DNA
<213> ORGANISM: Artificial Sequence
<220> FEATURE:
<223> OTHER INFORMATION: Synthetic DNA

<400> SEQUENCE: 13
gaatcctttg gtgccgtaaa      20

<210> SEQ ID NO 14
<211> LENGTH: 20
<212> TYPE: DNA
<213> ORGANISM: Artificial Sequence
<220> FEATURE:
<223> OTHER INFORMATION: Synthetic DNA

<400> SEQUENCE: 14
gtccatcgca gatctacccg      20

<210> SEQ ID NO 15
<211> LENGTH: 40
<212> TYPE: DNA
<213> ORGANISM: Artificial Sequence
<220> FEATURE:
<223> OTHER INFORMATION: Synthetic DNA

<400> SEQUENCE: 15
atagccccaa gtcaaaacag ttgaccttgg gtggctcgca      40

-continued

```
<210> SEQ ID NO 16
<211> LENGTH: 40
<212> TYPE: DNA
<213> ORGANISM: Artificial Sequence
<220> FEATURE:
<223> OTHER INFORMATION: Synthetic DNA

<400> SEQUENCE: 16
tgcgagccac ccaaggtcaa ctgttttgac ttggggctat            40

<210> SEQ ID NO 17
<211> LENGTH: 20
<212> TYPE: DNA
<213> ORGANISM: Artificial Sequence
<220> FEATURE:
<223> OTHER INFORMATION: Synthetic DNA

<400> SEQUENCE: 17
tagatacttc catgggtatg                                  20

<210> SEQ ID NO 18
<211> LENGTH: 5489
<212> TYPE: DNA
<213> ORGANISM: Corynebacterium glutamicum ATCC13032
<220> FEATURE:
<221> NAME/KEY: CDS
<222> LOCATION: (1001)..(1729)
<220> FEATURE:
<221> NAME/KEY: CDS
<222> LOCATION: (1847)..(2734)
<220> FEATURE:
<221> NAME/KEY: CDS
<222> LOCATION: (2856)..(3542)
<220> FEATURE:
<221> NAME/KEY: CDS
<222> LOCATION: (3668)..(4489)

<400> SEQUENCE: 18
acctcggtaa ctccctgatc caccagtgct tgtacctctg cgaggatgtc tcctggtcga     60
cggtcctgct ctttaccgcg cagcgacgga acgatgcaga aagtacaggt gttgttacat   120
ccgactgata cggacaccca accagcgtaa gcagactcgc gctttgcaga aagtactgac   180
gggaactgct cgagggaatc gacaatttcg acttccgctt gggcattgtg ctccgcgcgc   240
tgaagcaagg ttggcaagga accaatgttg tgggtaccaa acaccacgtc cacccacggt   300
gcttttttca ccacggtatc tttgtctttt tgagccaaac aaccaccgac agcgatttgc   360
atgcctgggt tctttttctt cacgctgcgc aggttgccca aagtgccata gaggcgcata   420
tcggcgtttt cacgcacggc gcacgtatta aatacgacaa gatccggagt ggtgtcctcc   480
ggagcagcaa cgtatccagc ctcctcgagc aggcccgaaa ggcgctcaga tcgtgcaca   540 ttcatctgac agccgtaggt ttttacctcg taggtgcgaa cctgcccctc tgcggtttct   600
gggagggtgg cttgaccggg atgttgattt acctttgcgt ggttcaattg ctgcgtcacg   660
gttgctcatt gtatccctgt tgcgcgagct gacataaacg cctatttagg actctgaact   720
aacaaggctc gtctccgacc ttgccttgag aattcctagg cttagcgaag tttaacttgg   780
ccacattcgc acgcttattt aacacgcaat atctatcatg tgataggtaa atttcggaca   840
ggatcggaga ctaccccaa accttgcccc ctaccgacct gcgaaaatgc tggtaaatgt   900
agtgctattt gtttcaaaat ggactcattc acacaattgc gaacattctc ggcacaaact   960
gctttaagct accccttatga cgcagaccac agaatccccg atg atc aag atg acg  1015
                                              Met Ile Lys Met Thr
                                              1               5
```

| | | |
|---|---|---|
| gga gtg caa aaa tac ttc ggc gac ttt cat gcc ctt acg gat att gat<br>Gly Val Gln Lys Tyr Phe Gly Asp Phe His Ala Leu Thr Asp Ile Asp<br>10                                     15                            20 | | 1063 |
| ctt gaa att ccc aga gga caa gtt gtc gtc gta ctt gga cca tcc gga<br>Leu Glu Ile Pro Arg Gly Gln Val Val Val Val Leu Gly Pro Ser Gly<br>25                                 30                           35 | | 1111 |
| tcc ggc aag tca acc ctt tgc cgc acg atc aac cgt ctc gaa acc atc<br>Ser Gly Lys Ser Thr Leu Cys Arg Thr Ile Asn Arg Leu Glu Thr Ile<br>40                               45                            50 | | 1159 |
| gag gaa ggc acc atc gaa atc gat gga aag gtt ctc cca gaa gaa ggt<br>Glu Glu Gly Thr Ile Glu Ile Asp Gly Lys Val Leu Pro Glu Glu Gly<br>55                               60                         65 | | 1207 |
| aaa ggc tta gcc aat ctc cgc gcc gat gtc gga atg gta ttc cag tcc<br>Lys Gly Leu Ala Asn Leu Arg Ala Asp Val Gly Met Val Phe Gln Ser<br>70                         75                           80                      85 | | 1255 |
| ttc aac ctc ttc ccc cac ctc acc atc aaa gac aac gtc act ctt gca<br>Phe Asn Leu Phe Pro His Leu Thr Ile Lys Asp Asn Val Thr Leu Ala<br>90                         95                           100 | | 1303 |
| ccc atc aaa gtg cga aag atg aaa aag tct gaa gcc gaa aag ctt gcg<br>Pro Ile Lys Val Arg Lys Met Lys Lys Ser Glu Ala Glu Lys Leu Ala<br>105                     110                   115 | | 1351 |
| atg agc ctg ttg gaa cgc gtc ggc atc gca aac caa gct gat aaa tat<br>Met Ser Leu Leu Glu Arg Val Gly Ile Ala Asn Gln Ala Asp Lys Tyr<br>120                   125                   130 | | 1399 |
| ccg gcg caa ctg tcc ggc ggt cag caa cag cgt gtg gcc atc gcg cgc<br>Pro Ala Gln Leu Ser Gly Gly Gln Gln Gln Arg Val Ala Ile Ala Arg<br>135                   140                   145 | | 1447 |
| gca ctt gcg atg aac cca aag atc atg ctt ttc gac gag ccc acc tcc<br>Ala Leu Ala Met Asn Pro Lys Ile Met Leu Phe Asp Glu Pro Thr Ser<br>150                   155                   160                   165 | | 1495 |
| gcc ctt gac cct gaa atg gtc aac gaa gtg ttg gac gtc atg gca agc<br>Ala Leu Asp Pro Glu Met Val Asn Glu Val Leu Asp Val Met Ala Ser<br>170                   175                   180 | | 1543 |
| ctt gcc aag gaa ggc atg acg atg gtg tgt gtt acc cac gag atg gga<br>Leu Ala Lys Glu Gly Met Thr Met Val Cys Val Thr His Glu Met Gly<br>185                   190                   195 | | 1591 |
| ttc gca cgc aaa gca gcc gat cgt gtg ttg ttc atg gcg gat ggg ctc<br>Phe Ala Arg Lys Ala Ala Asp Arg Val Leu Phe Met Ala Asp Gly Leu<br>200                   205                   210 | | 1639 |
| att gtg gaa gat acg gaa cca gat tcc ttc ttc acc aac cct aag tct<br>Ile Val Glu Asp Thr Glu Pro Asp Ser Phe Phe Thr Asn Pro Lys Ser<br>215                   220                   225 | | 1687 |
| gat cgt gca aaa gac ttc ctc ggc aag atc ctt gcc cac tag<br>Asp Arg Ala Lys Asp Phe Leu Gly Lys Ile Leu Ala His<br>230                   235                   240 | | 1729 |
| ttttcggctg cgcctctatc ttcagagtca cttctttcag tgtcattttt ctcggcccta | | 1789 |
| atcccccgct ggagttcaat cagcgattgc aaccttttag atatataagg agacaac | | 1846 |
| atg tct gca aag cgt act ttt acc cgt atc ggt gcg att ctt gga gca<br>Met Ser Ala Lys Arg Thr Phe Thr Arg Ile Gly Ala Ile Leu Gly Ala<br>245                   250                   255 | | 1894 |
| act gca ctt gcc gga gtt acc ctc acc gcc tgt ggt gat tca agc ggt<br>Thr Ala Leu Ala Gly Val Thr Leu Thr Ala Cys Gly Asp Ser Ser Gly<br>260                   265                   270 | | 1942 |
| ggc gac gga ttc ctc gca gcc att gaa aat ggt tct gtc aat gtc ggc<br>Gly Asp Gly Phe Leu Ala Ala Ile Glu Asn Gly Ser Val Asn Val Gly<br>275                   280                   285                   290 | | 1990 |
| acc aaa tac gat cag cct ggt ctt ggc ctc cgc aac cca gac aac tcc<br>Thr Lys Tyr Asp Gln Pro Gly Leu Gly Leu Arg Asn Pro Asp Asn Ser<br>295                   300                   305 | | 2038 |

```
atg agc ggt ctc gac gtg gat gtt gct gaa tac gta gtc aac tcc atc        2086
Met Ser Gly Leu Asp Val Asp Val Ala Glu Tyr Val Val Asn Ser Ile
        310                 315                 320 gct gat gac aag ggc tgg gat cac ccc acc atc gaa tgg cgt gaa tcc        2134
Ala Asp Asp Lys Gly Trp Asp His Pro Thr Ile Glu Trp Arg Glu Ser
                325                 330                 335 cct tct gcg cag cgt gaa acc ctc att caa aac ggt gag gta gac atg        2182
Pro Ser Ala Gln Arg Glu Thr Leu Ile Gln Asn Gly Glu Val Asp Met
    340                 345                 350 atc gca gca acc tac tcc atc aac gct ggc cgt tca gag tcc gtc aac        2230
Ile Ala Ala Thr Tyr Ser Ile Asn Ala Gly Arg Ser Glu Ser Val Asn
355                 360                 365                 370 ttc ggt ggc cca tac ctg ctt acc cac cag gct ctg ctt gtt cgc caa        2278
Phe Gly Gly Pro Tyr Leu Leu Thr His Gln Ala Leu Leu Val Arg Gln
                375                 380                 385 gat gac gat cgc att gaa acc ctc gag gac ttg gat aac ggt ttg atc        2326
Asp Asp Asp Arg Ile Glu Thr Leu Glu Asp Leu Asp Asn Gly Leu Ile
                390                 395                 400 ctg tgc tcc gtt tcc gga tcc act cca gct cag aag gtc aag gat gtc        2374
Leu Cys Ser Val Ser Gly Ser Thr Pro Ala Gln Lys Val Lys Asp Val
            405                 410                 415 ctc cca ggc gtt cag ctc caa gaa tac gac acc tac tct tcc tgt gtt        2422
Leu Pro Gly Val Gln Leu Gln Glu Tyr Asp Thr Tyr Ser Ser Cys Val
420                 425                 430 gag gca ctg tcc cag ggc aac gtt gac gcc ctg acc act gac gcc acc        2470
Glu Ala Leu Ser Gln Gly Asn Val Asp Ala Leu Thr Thr Asp Ala Thr
435                 440                 445                 450 atc ctc ttc ggc tac tcc cag cag tac gaa ggc gac ttc cgc gtt gtg        2518
Ile Leu Phe Gly Tyr Ser Gln Gln Tyr Glu Gly Asp Phe Arg Val Val
                455                 460                 465 gaa atg gaa aag gac ggc gag cca ttc acc gac gag tac tac ggc att        2566
Glu Met Glu Lys Asp Gly Glu Pro Phe Thr Asp Glu Tyr Tyr Gly Ile
                470                 475                 480 ggc ctg aag aag gat gac cag gaa ggc acc gac gct atc aac gcc gca        2614
Gly Leu Lys Lys Asp Asp Gln Glu Gly Thr Asp Ala Ile Asn Ala Ala
            485                 490                 495 ctt gag cgc atg tac gct gac ggc acc ttc cag cga ctg ctc acc gag        2662
Leu Glu Arg Met Tyr Ala Asp Gly Thr Phe Gln Arg Leu Leu Thr Glu
        500                 505                 510 aac ctc ggt gaa gac tcc gtg gtt gtt gaa gaa ggc acc cca ggt gac        2710
Asn Leu Gly Glu Asp Ser Val Val Val Glu Glu Gly Thr Pro Gly Asp
515                 520                 525                 530 ctc tcc ttc ctc gac gca agc tag tgtgacggct tttaaaagcc agctttaaga      2764
Leu Ser Phe Leu Asp Ala Ser
                535 aatgtgcgtg gcgcttaaaa ccccgaaagc gccacgcaca acccatttaa gttcatgatt    2824 tatttccatc cttaacaagg agcaccacca c atg agc act ttg tgg gcg gat        2876
                                  Met Ser Thr Leu Trp Ala Asp
                                                          540 ctg ggt ccg tct cta ctt cca gct ttt tgg gtg acc atc aaa ctc acc        2924
Leu Gly Pro Ser Leu Leu Pro Ala Phe Trp Val Thr Ile Lys Leu Thr
545                 550                 555                 560 att tat tcc gcc atc ggc gcc atg att ttc gga acc atc ctc acc aca        2972
Ile Tyr Ser Ala Ile Gly Ala Met Ile Phe Gly Thr Ile Leu Thr Thr
                565                 570                 575 atg agg gtc tcg ccc gtt aaa atc ctc cgc acg ttg tcc acg gcg tac        3020
Met Arg Val Ser Pro Val Lys Ile Leu Arg Thr Leu Ser Thr Ala Tyr
                580                 585                 590
```

```
atc aac aca gtc cga aat acc cca ctt act ctt gtg gtg ctg ttt tgc      3068
Ile Asn Thr Val Arg Asn Thr Pro Leu Thr Leu Val Val Leu Phe Cys
            595                 600                 605 tcc ttt ggc ctt tac caa aac ctc ggg ttg act ttg gcg ggc cgt gaa      3116
Ser Phe Gly Leu Tyr Gln Asn Leu Gly Leu Thr Leu Ala Gly Arg Glu
        610                 615                 620 agc tcc aca ttc ttg gtg gat aat aac ttc cgc ttg gcc gta ctt ggc      3164
Ser Ser Thr Phe Leu Val Asp Asn Asn Phe Arg Leu Ala Val Leu Gly
625                 630                 635                 640 ttc att ttg tac acc tca acc ttc gtt gcc gag tcc ctg cgt tcg ggt      3212
Phe Ile Leu Tyr Thr Ser Thr Phe Val Ala Glu Ser Leu Arg Ser Gly
            645                 650                 655 att aac acc gtg cac ttt ggg caa gca gaa gct gcg cgt tcc cta gga      3260
Ile Asn Thr Val His Phe Gly Gln Ala Glu Ala Ala Arg Ser Leu Gly
        660                 665                 670 ctg ggc ttt ggc gcg act ttc cgt tcc att att ttc ccg cag gct gtg      3308
Leu Gly Phe Gly Ala Thr Phe Arg Ser Ile Ile Phe Pro Gln Ala Val
    675                 680                 685 cgc gcc gcg atc gtc cct ttg ggc aac aca ctg atc gca ctg act aag      3356
Arg Ala Ala Ile Val Pro Leu Gly Asn Thr Leu Ile Ala Leu Thr Lys
690                 695                 700 aac acc acc atc gcc tct gtc att gga gtt ggc gaa gcc tcc ctg ctg      3404
Asn Thr Thr Ile Ala Ser Val Ile Gly Val Gly Glu Ala Ser Leu Leu
705                 710                 715                 720 atg aaa gcc acc atc gaa aat cac gcc aac atg cta ttt gtc gtg ttc      3452
Met Lys Ala Thr Ile Glu Asn His Ala Asn Met Leu Phe Val Val Phe
            725                 730                 735 gcg atc ttc gcc gtt ggc ttc atg att ctg acc ctg cct atg ggc ctt      3500
Ala Ile Phe Ala Val Gly Phe Met Ile Leu Thr Leu Pro Met Gly Leu
        740                 745                 750 ggc ttg ggc aaa ctc tct gag cgt ttg gcg gtg aag aag taa              3542
Gly Leu Gly Lys Leu Ser Glu Arg Leu Ala Val Lys Lys
    755                 760                 765 tggctaatac agttcgcgca acagtcctct acgatgctcc tggaccaaag ggccgtcgat     3602
tcaacctcat aatcaccatt ctcacggtgg ttctgggatt ggcgctcctc ttctggattg     3662 gctcc atg ctt tca ggc aac ggc caa ctc gat gcc aac aaa tgg act ccg    3712
      Met Leu Ser Gly Asn Gly Gln Leu Asp Ala Asn Lys Trp Thr Pro
          770                 775                 780 ttc atc aat tcc caa acc tgg acc acc tac att ctt cct ggt ttg tgg      3760
Phe Ile Asn Ser Gln Thr Trp Thr Thr Tyr Ile Leu Pro Gly Leu Trp
            785                 790                 795 ggc acg ctg aaa tct gcc gtg ttc tcg gtg atc ttg gct ctg gtc atg      3808
Gly Thr Leu Lys Ser Ala Val Phe Ser Val Ile Leu Ala Leu Val Met
        800                 805                 810 ggt acc gca ctg ggt ctt ggc cgt atc tct gaa atc agg att ctc cgc      3856
Gly Thr Ala Leu Gly Leu Gly Arg Ile Ser Glu Ile Arg Ile Leu Arg
    815                 820                 825 tgg ttc tgc gcc gtc atc atc gag act ttc cga gcc att ccg gtt ctg      3904
Trp Phe Cys Ala Val Ile Ile Glu Thr Phe Arg Ala Ile Pro Val Leu
830                 835                 840 atc ctc atg att ttc gcc tac cag atg ttc gcc cag tac aac atc gtg      3952
Ile Leu Met Ile Phe Ala Tyr Gln Met Phe Ala Gln Tyr Asn Ile Val
845                 850                 855                 860 ccg tcg agc cag ctc gcg ttc gcc gcc gtg gta ttc ggt ctg acc atg      4000
Pro Ser Ser Gln Leu Ala Phe Ala Ala Val Val Phe Gly Leu Thr Met
            865                 870                 875 tac aac ggt tct gtg atc gca gag att ctg cgt tct ggt atc gct tcc      4048
Tyr Asn Gly Ser Val Ile Ala Glu Ile Leu Arg Ser Gly Ile Ala Ser
        880                 885                 890
```

```
ctg cct aag ggg cag aag gaa gca gcg att gcg ttg ggt atg tct tct    4096
Leu Pro Lys Gly Gln Lys Glu Ala Ala Ile Ala Leu Gly Met Ser Ser
        895                 900                 905 agg caa acc acc tgg tca atc ttg ttg cct cag gcc gtg gct gca atg    4144
Arg Gln Thr Thr Trp Ser Ile Leu Leu Pro Gln Ala Val Ala Ala Met
    910                 915                 920 ctc cca gcg ttg atc tct cag atg gtt att gca ctg aag gac tcc gca    4192
Leu Pro Ala Leu Ile Ser Gln Met Val Ile Ala Leu Lys Asp Ser Ala
925                 930                 935                 940 ctt ggt tac cag atc ggc tac att gaa gtg gtt cgt tcc ggt att cag    4240
Leu Gly Tyr Gln Ile Gly Tyr Ile Glu Val Val Arg Ser Gly Ile Gln
            945                 950                 955 tcc gcg tct gtc aac cgc aac tac ctt gca gcg ctg ttt gtt gtt gcg    4288
Ser Ala Ser Val Asn Arg Asn Tyr Leu Ala Ala Leu Phe Val Val Ala
        960                 965                 970 ctg atc atg att gtt ctg aac ttc tcc ctc acc gct ctg gct tct cgc    4336
Leu Ile Met Ile Val Leu Asn Phe Ser Leu Thr Ala Leu Ala Ser Arg
    975                 980                 985 atc gag cgc cag ttg cgt gca ggt agg gct cgt aag   aac att gtt gcc    4384
Ile Glu Arg Gln Leu Arg Ala Gly Arg Ala Arg Lys   Asn Ile Val Ala
990                 995                 1000 aag gtc cct gag cag cca gat caa ggt ctg gag   acc aag gac aat       4429
Lys Val Pro Glu Gln Pro Asp Gln Gly Leu Glu   Thr Lys Asp Asn
1005                1010                          1015 gtc aat gtc gac tgg cag gat cct gat tat aag   gat ctg aaa acc       4474
Val Asn Val Asp Trp Gln Asp Pro Asp Tyr Lys   Asp Leu Lys Thr
1020                1025                          1030 cct gga gtt cag taa ctcccttacc ccggatgatt cccatccggg gtttagtttt    4529
Pro Gly Val Gln
1035 tcaaatcctc gattgcgcg tctagcgctt cccgcgcaag gtccatggac attccagccg    4589 gaaatcccg ccgtgccagc gcaccaacca cgcgccgaag cgctttgtcg tagtcggcgc    4649 ggtcctgcgg aatcttggtc tctgagcgcg ccttttcac ggccaccgcc cgcgccgtgt    4709 cccgctcatc ggcctggtcg atttgctcaa gcgccgcagc acgcgtttgc ttgtcgacgc    4769 cttttcctg cagttcgcgg tccagcgcac gcgaagattt cctcgcctg gcagcacgtt    4829 gccgaaccca ctcagtggca aaaacttcat catcaagcag tttggatctg gtgagatcgc    4889 caatgacctc attgatgatg tcttcctcaa actccagtgc tttaagtctg gtgcttagtt    4949 cgttgactga tcgtgcgcgt tggttaagca gcagcagggc acgtctgcgt acgttggctt    5009 tcttttcttc tttttcatgg tcaaagaagt ctgattcgcc tcgcgcatga gcgcgttcaa    5069 agttgtcgag tgcttttctg agcttttcaa tcttttcggc ttggatatcc atcgcgttgt    5129 tgcccttcgt tgacgaaaaa gcaggaacaa gccacatcat ggtttaagtg tgtggattgt    5189 ccctgctttg ttaaaactgg tgcttagtct tcagcgtctg cttcggtgtc ggcttcatca    5249 tcgaagtcaa cgttaggcac gagctctact ggatcgtcgg tgagttcatc tgaggctgca    5309 gcgtacttgc ctactcccag cttcttgaag atcttatctt ccagctcatc ggtgagttca    5369 gggttctcct tgagggaaag acgcaccttt tccttacctt gaccaagctg ttcgccctcg    5429 taggtgaacc aggaacctga cttcttcaca atgccgttgt ccactgccaa gtcaatgacg    5489
```

<210> SEQ ID NO 19
<211> LENGTH: 20
<212> TYPE: DNA
<213> ORGANISM: Artificial Sequence
<220> FEATURE:
<223> OTHER INFORMATION: Synthetic DNA

```
<400> SEQUENCE: 19
acctcggtaa ctccctgatc                                                    20

<210> SEQ ID NO 20
<211> LENGTH: 40
<212> TYPE: DNA
<213> ORGANISM: Artificial Sequence
<220> FEATURE:
<223> OTHER INFORMATION: Synthetic DNA

<400> SEQUENCE: 20
aatcatccgg ggtaagggag cggggattct gtggtctgcg                              40

<210> SEQ ID NO 21
<211> LENGTH: 40
<212> TYPE: DNA
<213> ORGANISM: Artificial Sequence
<220> FEATURE:
<223> OTHER INFORMATION: Synthetic DNA

<400> SEQUENCE: 21
cgcagaccac agaatccccg ctcccttacc ccggatgatt                              40

<210> SEQ ID NO 22
<211> LENGTH: 20
<212> TYPE: DNA
<213> ORGANISM: Artificial Sequence
<220> FEATURE:
<223> OTHER INFORMATION: Synthetic DNA

<400> SEQUENCE: 22
cgtcattgac ttggcagtgg                                                    20

<210> SEQ ID NO 23
<211> LENGTH: 20
<212> TYPE: DNA
<213> ORGANISM: Artificial Sequence
<220> FEATURE:
<223> OTHER INFORMATION: Synthetic DNA

<400> SEQUENCE: 23
gagactaccc ccaaaccttg                                                    20

<210> SEQ ID NO 24
<211> LENGTH: 40
<212> TYPE: DNA
<213> ORGANISM: Artificial Sequence
<220> FEATURE:
<223> OTHER INFORMATION: Synthetic DNA

<400> SEQUENCE: 24
ggcttttaaa agccgtcaca gttgtctcct tatatatcta                              40

<210> SEQ ID NO 25
<211> LENGTH: 40
<212> TYPE: DNA
<213> ORGANISM: Artificial Sequence
<220> FEATURE:
<223> OTHER INFORMATION: Synthetic DNA

<400> SEQUENCE: 25
tagatatata aggagacaac tgtgacggct tttaaaagcc                              40
```

```
<210> SEQ ID NO 26
<211> LENGTH: 20
<212> TYPE: DNA
<213> ORGANISM: Artificial Sequence
<220> FEATURE:
<223> OTHER INFORMATION: Synthetic DNA

<400> SEQUENCE: 26
gtccaggttt gggaattgat                                                    20

<210> SEQ ID NO 27
<211> LENGTH: 446
<212> TYPE: PRT
<213> ORGANISM: Corynebacterium glutamicum ATCC13032

<400> SEQUENCE: 27
```

Met Asn Ser Glu Gln Glu Phe Val Leu Ser Ala Ile Glu Glu Arg Asp
1               5                   10                  15

Ile Lys Phe Val Arg Leu Trp Phe Thr Asp Ile Leu Gly His Leu Lys
            20                  25                  30

Ser Val Val Ala Pro Ala Glu Leu Glu Ser Ala Leu Glu Glu Gly
        35                  40                  45

Ile Gly Phe Asp Gly Ser Ala Ile Glu Gly Tyr Ala Arg Ile Ser Glu
    50                  55                  60

Ala Asp Thr Ile Ala Arg Pro Asp Pro Ser Thr Phe Gln Val Leu Pro
65                  70                  75                  80

Leu Glu Ala Gly Ile Ser Lys Leu Gln Ala Ala Arg Leu Phe Cys Asp
                85                  90                  95

Val Thr Met Pro Asp Gly Gln Pro Ser Phe Ser Asp Pro Arg Gln Val
            100                 105                 110

Leu Arg Arg Gln Val Gln Leu Ala Ala Asp Glu Gly Leu Thr Cys Met
        115                 120                 125

Ile Ser Pro Glu Ile Glu Phe Tyr Leu Val Gln Ser Leu Arg Thr Asn
    130                 135                 140

Gly Leu Pro Pro Val Pro Thr Asp Asn Gly Gly Tyr Phe Asp Gln Ala
145                 150                 155                 160

Thr Phe Asn Glu Ala Pro Asn Phe Arg Arg Asn Ala Met Val Ala Leu
                165                 170                 175

Glu Glu Leu Gly Ile Pro Val Glu Phe Ser His His Glu Thr Ala Pro
            180                 185                 190

Gly Gln Gln Glu Ile Asp Leu Arg His Ala Asp Ala Leu Thr Met Ala
        195                 200                 205

Asp Asn Ile Met Thr Phe Arg Tyr Ile Met Lys Gln Val Ala Arg Asp
    210                 215                 220

Gln Gly Val Gly Ala Ser Phe Met Pro Lys Pro Phe Gln Glu His Ala
225                 230                 235                 240

Gly Ser Ala Met His Thr His Met Ser Leu Phe Glu Gly Asp Thr Asn
                245                 250                 255

Ala Phe His Asp Pro Asp Asp Ser Tyr Met Leu Ser Lys Thr Ala Lys
            260                 265                 270

Gln Phe Ile Ala Gly Ile Leu His His Ala Pro Glu Phe Thr Ala Val
        275                 280                 285

Thr Asn Gln Trp Val Asn Ser Tyr Lys Arg Ile Val Tyr Gly Asn Glu
    290                 295                 300

Ala Pro Thr Ala Ala Thr Trp Gly Val Ser Asn Arg Ser Ala Leu Val
305                 310                 315                 320

```
Arg Val Pro Thr Tyr Arg Leu Asn Lys Glu Glu Ser Arg Arg Val Glu
            325                 330                 335

Val Arg Leu Pro Asp Thr Ala Cys Asn Pro Tyr Leu Ala Phe Ser Val
            340                 345                 350

Met Leu Gly Ala Gly Leu Lys Gly Ile Lys Glu Gly Tyr Glu Leu Asp
            355                 360                 365

Glu Pro Ala Glu Asp Asp Ile Ser Asn Leu Ser Phe Arg Glu Arg Arg
            370                 375                 380

Ala Met Gly Tyr Asn Asp Leu Pro Ser Ser Leu Asp Gln Ala Leu Arg
385                 390                 395                 400

Gln Met Glu Lys Ser Glu Leu Val Ala Asp Ile Leu Gly Glu His Val
            405                 410                 415

Phe Glu Phe Phe Leu Arg Asn Lys Trp Arg Glu Trp Arg Asp Tyr Gln
            420                 425                 430

Glu Gln Ile Thr Pro Trp Glu Leu Arg Asn Asn Leu Asp Tyr
            435                 440                 445

<210> SEQ ID NO 28
<211> LENGTH: 1341
<212> TYPE: DNA
<213> ORGANISM: Corynebacterium glutamicum ATCC13032
<220> FEATURE:
<221> NAME/KEY: CDS
<222> LOCATION: (1)..(1338)

<400> SEQUENCE: 28 atg aac agc gaa cag gaa ttt gta ctc agc gcc att gaa gaa cgc gac      48
Met Asn Ser Glu Gln Glu Phe Val Leu Ser Ala Ile Glu Glu Arg Asp
1               5                   10                  15 att aag ttt gtg cgt cta tgg ttc act gac att ctt ggc cac ttg aag      96
Ile Lys Phe Val Arg Leu Trp Phe Thr Asp Ile Leu Gly His Leu Lys
                20                  25                  30 tca gtg gtt gtg gct cct gca gaa cta gag tct gcg ttg gaa gaa ggc     144
Ser Val Val Val Ala Pro Ala Glu Leu Glu Ser Ala Leu Glu Glu Gly
            35                  40                  45 atc gga ttc gat ggc tca gcc att gag ggc tac gcg cgt atc tcg gaa     192
Ile Gly Phe Asp Gly Ser Ala Ile Glu Gly Tyr Ala Arg Ile Ser Glu
        50                  55                  60 gcg gac acc att gcc cgc cca gat cca tcg aca ttc cag gtc ctc cca     240
Ala Asp Thr Ile Ala Arg Pro Asp Pro Ser Thr Phe Gln Val Leu Pro
65                  70                  75                  80 cta gaa gcg ggc atc tca aaa ctg cag gca gca cgc ctg ttt tgc gat     288
Leu Glu Ala Gly Ile Ser Lys Leu Gln Ala Ala Arg Leu Phe Cys Asp
                85                  90                  95 gtc acg atg cca gac gga cag cca tct ttt tct gac ccg cgc caa gtg     336
Val Thr Met Pro Asp Gly Gln Pro Ser Phe Ser Asp Pro Arg Gln Val
                100                 105                 110 ctg cgc agg cag gtc caa cta gct gca gat gaa ggc ttg acc tgc atg     384
Leu Arg Arg Gln Val Gln Leu Ala Ala Asp Glu Gly Leu Thr Cys Met
            115                 120                 125 atc tca cca gag att gag ttc tat ttg gtg caa agc ctt cgc acc aac     432
Ile Ser Pro Glu Ile Glu Phe Tyr Leu Val Gln Ser Leu Arg Thr Asn
        130                 135                 140 gga ctg cca cct gtg ccc act gac aac gga gga tat ttc gac caa gcc     480
Gly Leu Pro Pro Val Pro Thr Asp Asn Gly Gly Tyr Phe Asp Gln Ala
145                 150                 155                 160 aca ttc aat gag gcg ccg aat ttc cgt cga aac gcg atg gta gcg ctg     528
Thr Phe Asn Glu Ala Pro Asn Phe Arg Arg Asn Ala Met Val Ala Leu
                165                 170                 175
```

```
gag gaa ctc ggc atc cct gtc gag ttc tcc cac cat gaa act gca cct    576
Glu Glu Leu Gly Ile Pro Val Glu Phe Ser His His Glu Thr Ala Pro
            180                 185                 190 ggc cag caa gaa atc gat tta cgc cat gcg gat gcg ctc acc atg gcc    624
Gly Gln Gln Glu Ile Asp Leu Arg His Ala Asp Ala Leu Thr Met Ala
        195                 200                 205 gac aac atc atg acc ttc cgc tac atc atg aaa cag gtg gca agg gac    672
Asp Asn Ile Met Thr Phe Arg Tyr Ile Met Lys Gln Val Ala Arg Asp
    210                 215                 220 caa ggc gtc ggg gca tca ttt atg ccc aag cca ttc caa gaa cat gca    720
Gln Gly Val Gly Ala Ser Phe Met Pro Lys Pro Phe Gln Glu His Ala
225                 230                 235                 240 ggc tcc gcc atg cac acg cac atg tcc tta ttt gag ggc gat acc aac    768
Gly Ser Ala Met His Thr His Met Ser Leu Phe Glu Gly Asp Thr Asn
                245                 250                 255 gcg ttc cac gat cca gac gat tct tac atg ctg tcc aaa acc gca aaa    816
Ala Phe His Asp Pro Asp Asp Ser Tyr Met Leu Ser Lys Thr Ala Lys
            260                 265                 270 cag ttc atc gct gga atc ttg cat cac gct cca gaa ttc acc gct gtg    864
Gln Phe Ile Ala Gly Ile Leu His His Ala Pro Glu Phe Thr Ala Val
        275                 280                 285 acc aac cag tgg gtc aat tcc tac aaa cgc atc gtg tac gga aac gaa    912
Thr Asn Gln Trp Val Asn Ser Tyr Lys Arg Ile Val Tyr Gly Asn Glu
    290                 295                 300 gct cca act gcg gca acc tgg ggt gta tct aat cgt tct gcg ctg gtt    960
Ala Pro Thr Ala Ala Thr Trp Gly Val Ser Asn Arg Ser Ala Leu Val
305                 310                 315                 320 cgt gtt cct acc tac cgt ttg aat aag gag gag tcg cgc cgg gtg gag   1008
Arg Val Pro Thr Tyr Arg Leu Asn Lys Glu Glu Ser Arg Arg Val Glu
                325                 330                 335 gtg cgt ctt cct gat acc gct tgt aac cca tat ttg gcg ttt tca gtg   1056
Val Arg Leu Pro Asp Thr Ala Cys Asn Pro Tyr Leu Ala Phe Ser Val
            340                 345                 350 atg ctc ggc gct ggt ttg aaa ggc att aaa gaa ggt tat gag ctc gac   1104
Met Leu Gly Ala Gly Leu Lys Gly Ile Lys Glu Gly Tyr Glu Leu Asp
        355                 360                 365 gag cca gct gag gac gat atc tcc aac ttg agc ttc cgg gaa cgt cgc   1152
Glu Pro Ala Glu Asp Asp Ile Ser Asn Leu Ser Phe Arg Glu Arg Arg
    370                 375                 380 gcc atg ggc tac aac gat ctg cca agc agc ctt gat cag gca ctg cgc   1200
Ala Met Gly Tyr Asn Asp Leu Pro Ser Ser Leu Asp Gln Ala Leu Arg
385                 390                 395                 400 caa atg gaa aag tca gag ctt gtt gct gac atc ctc ggt gag cac gtt   1248
Gln Met Glu Lys Ser Glu Leu Val Ala Asp Ile Leu Gly Glu His Val
                405                 410                 415 ttt gag ttt ttc ttg cgc aat aag tgg cgt gaa tgg cgt gac tac caa   1296
Phe Glu Phe Phe Leu Arg Asn Lys Trp Arg Glu Trp Arg Asp Tyr Gln
            420                 425                 430 gag cag atc act ccg tgg gag ctc cga aac aat ctt gat tac tag       1341
Glu Gln Ile Thr Pro Trp Glu Leu Arg Asn Asn Leu Asp Tyr
        435                 440                 445

<210> SEQ ID NO 29
<211> LENGTH: 1844
<212> TYPE: DNA
<213> ORGANISM: Corynebacterium glutamicum ATCC13032
<220> FEATURE:
<221> NAME/KEY: CDS
<222> LOCATION: (501)..(1838)
```

<400> SEQUENCE: 29

```
tacttagctt cggtagctcg gtgagaatct tctccagggt catcaccggc aagtggctag      60
tttcggcggc acgcgttccg ttcacccaca gtgtgtacat ctcatcggag caggagtaag     120
caatctcagg tagcgcgtga acaggagtg gatcaatatc ggcggaaaac tcatggcgga     180
gatcggcggg agtccaccca cgaagcgcac agaaacctag gtggctgatg atgctttctt     240
ctaaaatctg acggtaagag tcttgtgcgt cggtgacgtt gtcggagaag tgggagagag     300
tcattgcggt ttccttattc gtaggagtgt tctaatttcg gtgcggttct cagtgaacca     360
cccaagctgg acacctccca ccccgtgtc atcaaaaaac cgcgacatcc ttgagtaact     420
ctgagaaaaa ctaccccga tgggagtata aaagtggcaa atgcgcagtc gatgtcccat     480
cgctgcgtag attagttttc atg aac agc gaa cag gaa ttt gta ctc agc gcc    533
                       Met Asn Ser Glu Gln Glu Phe Val Leu Ser Ala
                         1               5                  10 att gaa gaa cgc gac att aag ttt gtg cgt cta tgg ttc act gac att      581
Ile Glu Glu Arg Asp Ile Lys Phe Val Arg Leu Trp Phe Thr Asp Ile
         15                  20                  25 ctt ggc cac ttg aag tca gtg gtt gtg gct cct gca gaa cta gag tct      629
Leu Gly His Leu Lys Ser Val Val Val Ala Pro Ala Glu Leu Glu Ser
     30                  35                  40 gcg ttg gaa gaa ggc atc gga ttc gat ggc tca gcc att gag ggc tac      677
Ala Leu Glu Glu Gly Ile Gly Phe Asp Gly Ser Ala Ile Glu Gly Tyr
 45                  50                  55 gcg cgt atc tcg gaa gcg gac acc att gcc cgc cca gat cca tcg aca      725
Ala Arg Ile Ser Glu Ala Asp Thr Ile Ala Arg Pro Asp Pro Ser Thr
 60                  65                  70                  75 ttc cag gtc ctc cca cta gaa gcg ggc atc tca aaa ctg cag gca gca      773
Phe Gln Val Leu Pro Leu Glu Ala Gly Ile Ser Lys Leu Gln Ala Ala
             80                  85                  90 cgc ctg ttt tgc gat gtc acg atg cca gac gga cag cca tct ttt tct      821
Arg Leu Phe Cys Asp Val Thr Met Pro Asp Gly Gln Pro Ser Phe Ser
         95                 100                 105 gac ccg cgc caa gtg ctg cgc agg cag gtc caa cta gct gca gat gaa      869
Asp Pro Arg Gln Val Leu Arg Arg Gln Val Gln Leu Ala Ala Asp Glu
     110                 115                 120 ggc ttg acc tgc atg atc tca cca gag att gag ttc tat ttg gtg caa      917
Gly Leu Thr Cys Met Ile Ser Pro Glu Ile Glu Phe Tyr Leu Val Gln
 125                 130                 135 agc ctt cgc acc aac gga ctg cca cct gtg ccc act gac aac ggc gga      965
Ser Leu Arg Thr Asn Gly Leu Pro Pro Val Pro Thr Asp Asn Gly Gly
 140                 145                 150                 155 tat ttc gac caa gcc aca ttc aat gag gcg ccg aat ttc cgt cga aac     1013
Tyr Phe Asp Gln Ala Thr Phe Asn Glu Ala Pro Asn Phe Arg Arg Asn
             160                 165                 170 gcg atg gta gcg ctg gag gaa ctc ggc atc cct gtc gag ttc tcc cac     1061
Ala Met Val Ala Leu Glu Glu Leu Gly Ile Pro Val Glu Phe Ser His
         175                 180                 185 cat gaa act gca cct ggc cag caa gaa atc gat tta cgc cat gcg gat     1109
His Glu Thr Ala Pro Gly Gln Gln Glu Ile Asp Leu Arg His Ala Asp
     190                 195                 200 gcg ctc acc atg gcc gac aac atc atg acc ttc cgc tac atc atg aaa     1157
Ala Leu Thr Met Ala Asp Asn Ile Met Thr Phe Arg Tyr Ile Met Lys
 205                 210                 215 cag gtg gca agg gac caa ggc gtc ggg gca tca ttt atg ccc aag cca     1205
Gln Val Ala Arg Asp Gln Gly Val Gly Ala Ser Phe Met Pro Lys Pro
 220                 225                 230                 235
```

```
ttc caa gaa cat gca ggc tcc gcc atg cac acg cac atg tcc tta ttt      1253
Phe Gln Glu His Ala Gly Ser Ala Met His Thr His Met Ser Leu Phe
            240                 245                 250 gag ggc gat acc aac gcg ttc cac gat cca gac gat tct tac atg ctg      1301
Glu Gly Asp Thr Asn Ala Phe His Asp Pro Asp Asp Ser Tyr Met Leu
        255                 260                 265 tcc aaa acc gca aaa cag ttc atc gct gga atc ttg cat cac gct cca      1349
Ser Lys Thr Ala Lys Gln Phe Ile Ala Gly Ile Leu His His Ala Pro
    270                 275                 280 gaa ttc acc gct gtg acc aac cag tgg gtc aat tcc tac aaa cgc atc      1397
Glu Phe Thr Ala Val Thr Asn Gln Trp Val Asn Ser Tyr Lys Arg Ile
285                 290                 295 gtg tac gga aac gaa gct cca act gcg gca acc tgg ggt gta tct aat      1445
Val Tyr Gly Asn Glu Ala Pro Thr Ala Ala Thr Trp Gly Val Ser Asn
300                 305                 310                 315 cgt tct gcg ctg gtt cgt gtt cct acc tac cgt ttg aat aag gag gag      1493
Arg Ser Ala Leu Val Arg Val Pro Thr Tyr Arg Leu Asn Lys Glu Glu
                320                 325                 330 tcg cgc cgg gtg gag gtg cgt ctt cct gat acc gct tgt aac cca tat      1541
Ser Arg Arg Val Glu Val Arg Leu Pro Asp Thr Ala Cys Asn Pro Tyr
            335                 340                 345 ttg gcg ttt tca gtg atg ctc ggc gct ggt ttg aaa ggc att aaa gaa      1589
Leu Ala Phe Ser Val Met Leu Gly Ala Gly Leu Lys Gly Ile Lys Glu
        350                 355                 360 ggt tat gag ctc gac gag cca gct gag gac gat atc tcc aac ttg agc      1637
Gly Tyr Glu Leu Asp Glu Pro Ala Glu Asp Asp Ile Ser Asn Leu Ser
    365                 370                 375 ttc cgg gaa cgt cgc gcc atg ggc tac aac gat ctg cca agc agc ctt      1685
Phe Arg Glu Arg Arg Ala Met Gly Tyr Asn Asp Leu Pro Ser Ser Leu
380                 385                 390                 395 gat cag gca ctg cgc caa atg gaa aag tca gag ctt gtt gct gac atc      1733
Asp Gln Ala Leu Arg Gln Met Glu Lys Ser Glu Leu Val Ala Asp Ile
                400                 405                 410 ctc ggt gag cac gtt ttt gag ttt ttc ttg cgc aat aag tgg cgt gaa      1781
Leu Gly Glu His Val Phe Glu Phe Phe Leu Arg Asn Lys Trp Arg Glu
            415                 420                 425 tgg cgt gac tac caa gag cag atc act ccg tgg gag ctc cga aac aat      1829
Trp Arg Asp Tyr Gln Glu Gln Ile Thr Pro Trp Glu Leu Arg Asn Asn
        430                 435                 440 ctt gat tac tagact                                                   1844
Leu Asp Tyr
    445

<210> SEQ ID NO 30
<211> LENGTH: 29
<212> TYPE: DNA
<213> ORGANISM: Artificial Sequence
<220> FEATURE:
<223> OTHER INFORMATION: Synthetic DNA

<400> SEQUENCE: 30
tttggatcca aactcatggc ggagatcgg                                       29

<210> SEQ ID NO 31
<211> LENGTH: 21
<212> TYPE: DNA
<213> ORGANISM: Artificial Sequence
<220> FEATURE:
<223> OTHER INFORMATION: Synthetic DNA

<400> SEQUENCE: 31
gcgtatctcg aaagcggaca c                                               21
```

<210> SEQ ID NO 32
<211> LENGTH: 21
<212> TYPE: DNA
<213> ORGANISM: Artificial Sequence
<220> FEATURE:
<223> OTHER INFORMATION: Synthetic DNA

<400> SEQUENCE: 32
gtgtccgctt tcgagatacg c					21

<210> SEQ ID NO 33
<211> LENGTH: 29
<212> TYPE: DNA
<213> ORGANISM: Artificial Sequence
<220> FEATURE:
<223> OTHER INFORMATION: Synthetic DNA

<400> SEQUENCE: 33
tttggatccg gcttgggcat aaatgatgc					29

<210> SEQ ID NO 34
<211> LENGTH: 29
<212> TYPE: DNA
<213> ORGANISM: Artificial Sequence
<220> FEATURE:
<223> OTHER INFORMATION: Synthetic DNA

<400> SEQUENCE: 34
tttggatcct acttagcttc ggtagctcg					29

<210> SEQ ID NO 35
<211> LENGTH: 29
<212> TYPE: DNA
<213> ORGANISM: Artificial Sequence
<220> FEATURE:
<223> OTHER INFORMATION: Synthetic DNA

<400> SEQUENCE: 35
tttggatcca gtctagtaat caagattgt					29

<210> SEQ ID NO 36
<211> LENGTH: 640
<212> TYPE: PRT
<213> ORGANISM: Corynebacterium glutamicum ATCC13032

<400> SEQUENCE: 36

Met Cys Gly Leu Leu Gly Ile Leu Thr Ala Asn Gly Asn Ala Glu Ala
1               5                   10                  15

Phe Val Pro Ala Leu Glu Arg Ala Leu Pro Cys Met Arg His Arg Gly
                20                  25                  30

Pro Asp Asp Ala Gly Thr Trp His Asp Ala Asp Ala Ala Phe Gly Phe
            35                  40                  45

Asn Arg Leu Ser Ile Ile Asp Ile Ala His Ser His Gln Pro Leu Arg
        50                  55                  60

Trp Gly Pro Ala Asp Glu Pro Asp Arg Tyr Ala Met Thr Phe Asn Gly
65                  70                  75                  80

Glu Ile Tyr Asn Tyr Val Glu Leu Arg Lys Glu Leu Ser Asp Leu Gly
                85                  90                  95

Tyr Ala Phe Asn Thr Ser Gly Asp Gly Glu Pro Ile Val Val Gly Phe
                100                 105                 110

His His Trp Gly Glu Ser Val Val Glu His Leu Arg Gly Met Phe Gly
            115                 120                 125

```
Ile Ala Ile Trp Asp Thr Lys Glu Lys Ser Leu Phe Leu Ala Arg Asp
        130                 135                 140

Gln Phe Gly Ile Lys Pro Leu Phe Tyr Ala Thr Glu His Gly Thr
145                 150                 155                 160

Val Phe Ser Ser Glu Lys Lys Thr Ile Leu Glu Met Ala Glu Met
                165                 170                 175

Asn Leu Asp Leu Gly Leu Asp Lys Arg Thr Ile Glu His Tyr Val Asp
                180                 185                 190

Leu Gln Tyr Val Pro Glu Pro Asp Thr Leu His Ala Gln Ile Ser Arg
            195                 200                 205

Leu Glu Ser Gly Cys Thr Ala Thr Val Arg Pro Gly Gly Lys Leu Glu
        210                 215                 220

Gln Lys Arg Tyr Phe Lys Pro Gln Phe Pro Val Gln Lys Val Val Lys
225                 230                 235                 240

Gly Lys Glu Gln Asp Leu Phe Asp Arg Ile Ala Gln Val Leu Glu Asp
                245                 250                 255

Ser Val Glu Lys His Met Arg Ala Asp Val Thr Val Gly Ser Phe Leu
                260                 265                 270

Ser Gly Gly Ile Asp Ser Thr Ala Ile Ala Ala Leu Ala Lys Arg His
                275                 280                 285

Asn Pro Asp Leu Leu Thr Phe Thr Thr Gly Phe Glu Arg Glu Gly Tyr
290                 295                 300

Ser Glu Val Asp Val Ala Ala Glu Ser Ala Ala Ala Ile Gly Ala Glu
305                 310                 315                 320

His Ile Val Lys Ile Val Ser Pro Glu Glu Tyr Ala Asn Ala Ile Pro
                325                 330                 335

Lys Ile Met Trp Tyr Leu Asp Asp Pro Val Ala Asp Pro Ser Leu Val
                340                 345                 350

Pro Leu Tyr Phe Val Ala Ala Glu Ala Arg Lys His Val Lys Val Val
            355                 360                 365

Leu Ser Gly Glu Gly Ala Asp Glu Leu Phe Gly Gly Tyr Thr Ile Tyr
        370                 375                 380

Lys Glu Pro Leu Ser Leu Ala Pro Phe Glu Lys Ile Pro Ser Pro Leu
385                 390                 395                 400

Arg Lys Gly Leu Gly Lys Leu Ser Lys Val Leu Pro Asp Gly Met Lys
                405                 410                 415

Gly Lys Ser Leu Leu Glu Arg Gly Ser Met Thr Met Glu Glu Arg Tyr
                420                 425                 430

Tyr Gly Asn Ala Arg Ser Phe Asn Phe Glu Gln Met Gln Arg Val Ile
            435                 440                 445

Pro Trp Ala Lys Arg Glu Trp Asp His Arg Glu Val Thr Ala Pro Ile
450                 455                 460

Tyr Ala Gln Ser Arg Asn Phe Asp Pro Val Ala Arg Met Gln His Leu
465                 470                 475                 480

Asp Leu Phe Thr Trp Met Arg Gly Asp Ile Leu Val Lys Ala Asp Lys
                485                 490                 495

Ile Asn Met Ala Asn Ser Leu Glu Leu Arg Val Pro Phe Leu Asp Lys
                500                 505                 510

Glu Val Phe Lys Val Ala Glu Thr Ile Pro Tyr Asp Leu Lys Ile Ala
                515                 520                 525

Asn Gly Thr Thr Lys Tyr Ala Leu Arg Arg Ala Leu Glu Gln Ile Val
        530                 535                 540

Pro Pro His Val Leu His Arg Lys Lys Leu Gly Phe Pro Val Pro Met
545                 550                 555                 560
```

```
Arg His Trp Leu Ala Gly Asp Glu Leu Phe Gly Trp Ala Gln Asp Thr
                565                 570                 575

Ile Lys Glu Ser Gly Thr Glu Asp Ile Phe Asn Lys Gln Ala Val Leu
            580                 585                 590

Asp Met Leu Asn Glu His Arg Asp Gly Val Ser Asp His Ser Arg Arg
        595                 600                 605

Leu Trp Thr Val Leu Ser Phe Met Val Trp His Gly Ile Phe Val Glu
    610                 615                 620

Asn Arg Ile Asp Pro Gln Ile Glu Asp Arg Ser Tyr Pro Val Glu Leu
625                 630                 635                 640

<210> SEQ ID NO 37
<211> LENGTH: 1923
<212> TYPE: DNA
<213> ORGANISM: Corynebacterium glutamicum ATCC13032
<220> FEATURE:
<221> NAME/KEY: CDS
<222> LOCATION: (1)..(1920)

<400> SEQUENCE: 37 atg tgc ggc ctt ctt ggc ata ttg act gca aat ggg aac gct gaa gca      48
Met Cys Gly Leu Leu Gly Ile Leu Thr Ala Asn Gly Asn Ala Glu Ala
1               5                  10                  15 ttc gtt cct gca ctc gag cgg gcc ttg cca tgc atg cgc cac cgt ggt      96
Phe Val Pro Ala Leu Glu Arg Ala Leu Pro Cys Met Arg His Arg Gly
            20                  25                  30 cct gac gat gcc ggc act tgg cat gac gcc gat gca gcg ttt gga ttc     144
Pro Asp Asp Ala Gly Thr Trp His Asp Ala Asp Ala Ala Phe Gly Phe
        35                  40                  45 aac cgc ctc tcc atc att gat att gca cac tcc cac caa cca ctg cgt     192
Asn Arg Leu Ser Ile Ile Asp Ile Ala His Ser His Gln Pro Leu Arg
    50                  55                  60 tgg gga cct gcg gat gaa ccc gac cgc tac gca atg act ttc aac ggt     240
Trp Gly Pro Ala Asp Glu Pro Asp Arg Tyr Ala Met Thr Phe Asn Gly
65                  70                  75                  80 gag atc tac aac tac gtt gag ctg cgt aaa gag ctc tcg gat ttg gga     288
Glu Ile Tyr Asn Tyr Val Glu Leu Arg Lys Glu Leu Ser Asp Leu Gly
                85                  90                  95 tat gcc ttt aat act tct ggc gat ggc gag cca att gtt gtc ggt ttc     336
Tyr Ala Phe Asn Thr Ser Gly Asp Gly Glu Pro Ile Val Val Gly Phe
            100                 105                 110 cac cac tgg ggc gag tcc gtg gtc gag cat ctc cgc gga atg ttc ggc     384
His His Trp Gly Glu Ser Val Val Glu His Leu Arg Gly Met Phe Gly
        115                 120                 125 att gcc att tgg gat aca aag gaa aag tcg ctt ttc ctt gcg cgt gat     432
Ile Ala Ile Trp Asp Thr Lys Glu Lys Ser Leu Phe Leu Ala Arg Asp
    130                 135                 140 cag ttc ggc att aag cca ctg ttc tac gca acc acc gag cat ggc acc     480
Gln Phe Gly Ile Lys Pro Leu Phe Tyr Ala Thr Thr Glu His Gly Thr
145                 150                 155                 160 gtg ttc tcc tca gag aag aag acc atc ttg gag atg gcc gag gag atg     528
Val Phe Ser Ser Glu Lys Lys Thr Ile Leu Glu Met Ala Glu Glu Met
                165                 170                 175 aat cta gat ctg ggc ctt gat aag cgc acc att gag cac tac gtg gac     576
Asn Leu Asp Leu Gly Leu Asp Lys Arg Thr Ile Glu His Tyr Val Asp
            180                 185                 190 ttg cag tac gtg ccc gag cca gat acc ctt cac gcg cag att tcc cgc     624
Leu Gln Tyr Val Pro Glu Pro Asp Thr Leu His Ala Gln Ile Ser Arg
        195                 200                 205
```

```
ttg gag tca ggc tgc acc gca aca gtt cgt ccg ggc ggc aag ctg gaa      672
Leu Glu Ser Gly Cys Thr Ala Thr Val Arg Pro Gly Gly Lys Leu Glu
    210             215                 220 cag aag cgt tac ttc aag cct cag ttc cca gta cag aag gtc gta aag      720
Gln Lys Arg Tyr Phe Lys Pro Gln Phe Pro Val Gln Lys Val Val Lys
225             230                 235                 240 ggt aag gag cag gac ctc ttc gat cgc att gcc cag gtg ttg gag gat      768
Gly Lys Glu Gln Asp Leu Phe Asp Arg Ile Ala Gln Val Leu Glu Asp
                245                 250                 255 agc gtc gaa aag cat atg cgt gcc gac gtg acc gta ggc tcg ttc ctt      816
Ser Val Glu Lys His Met Arg Ala Asp Val Thr Val Gly Ser Phe Leu
        260                 265                 270 tcc ggc ggc att gac tca acc gca att gcg gcg ctt gca aag cgc cac      864
Ser Gly Gly Ile Asp Ser Thr Ala Ile Ala Ala Leu Ala Lys Arg His
    275                 280                 285 aac cct gac ctg ctc acc ttc acc acc ggt ttc gag cgt gaa ggc tac      912
Asn Pro Asp Leu Leu Thr Phe Thr Thr Gly Phe Glu Arg Glu Gly Tyr
290                 295                 300 tcg gag gtc gat gtg gct gcg gag tcc gcc gct gcg att ggc gct gag      960
Ser Glu Val Asp Val Ala Ala Glu Ser Ala Ala Ala Ile Gly Ala Glu
305             310                 315                 320 cac atc gtg aag att gtc tcg cct gag gaa tac gcc aac gcg att cct     1008
His Ile Val Lys Ile Val Ser Pro Glu Glu Tyr Ala Asn Ala Ile Pro
                325                 330                 335 aag atc atg tgg tac ttg gat gat cct gta gct gac cca tca ttg gtc     1056
Lys Ile Met Trp Tyr Leu Asp Asp Pro Val Ala Asp Pro Ser Leu Val
            340                 345                 350 ccg ctg tac ttc gtg gca gcg gaa gca cgt aag cac gtc aag gtt gtg     1104
Pro Leu Tyr Phe Val Ala Ala Glu Ala Arg Lys His Val Lys Val Val
        355                 360                 365 ctg tct ggc gag ggc gca gat gag ctg ttc ggt gga tac acc att tac     1152
Leu Ser Gly Glu Gly Ala Asp Glu Leu Phe Gly Gly Tyr Thr Ile Tyr
    370                 375                 380 aag gag ccg cta tcg ctt gct cca ttt gag aag atc cct tcc cca cta     1200
Lys Glu Pro Leu Ser Leu Ala Pro Phe Glu Lys Ile Pro Ser Pro Leu
385                 390                 395                 400 cgt aaa ggc ctg gga aag ctc agc aag gtt ctg cca gac ggc atg aag     1248
Arg Lys Gly Leu Gly Lys Leu Ser Lys Val Leu Pro Asp Gly Met Lys
                405                 410                 415 ggc aag tcc ctt ctt gag cgt ggc tcc atg acc atg gaa gag cgc tac     1296
Gly Lys Ser Leu Leu Glu Arg Gly Ser Met Thr Met Glu Glu Arg Tyr
            420                 425                 430 tac ggc aac gct cgc tcc ttc aat ttc gag cag atg caa cgc gtt att     1344
Tyr Gly Asn Ala Arg Ser Phe Asn Phe Glu Gln Met Gln Arg Val Ile
        435                 440                 445 cca tgg gca aag cgc gaa tgg gac cac cgc gaa gtc act gcg ccg atc     1392
Pro Trp Ala Lys Arg Glu Trp Asp His Arg Glu Val Thr Ala Pro Ile
    450                 455                 460 tac gca cag tcc cgc aac ttt gat cca gta gcc cgc atg caa cac ctg     1440
Tyr Ala Gln Ser Arg Asn Phe Asp Pro Val Ala Arg Met Gln His Leu
465                 470                 475                 480 gat ctg ttc acc tgg atg cgc ggc gac atc ctg gtc aag gct gac aag     1488
Asp Leu Phe Thr Trp Met Arg Gly Asp Ile Leu Val Lys Ala Asp Lys
                485                 490                 495 atc aac atg gcg aac tcc ctt gag ctg cga gtt cca ttc ttg gat aag     1536
Ile Asn Met Ala Asn Ser Leu Glu Leu Arg Val Pro Phe Leu Asp Lys
            500                 505                 510 gaa gtt ttc aag gtt gca gag acc att cct tac gac ctg aag att gcc     1584
Glu Val Phe Lys Val Ala Glu Thr Ile Pro Tyr Asp Leu Lys Ile Ala
        515                 520                 525
```

```
aac ggt acc acc aag tac gcg ctg cgc agg gca ctc gag cag att gtt      1632
Asn Gly Thr Thr Lys Tyr Ala Leu Arg Arg Ala Leu Glu Gln Ile Val
    530                 535                 540 ccg cct cac gtt ttg cac cgc aag aag ctg ggc ttc cct gtt ccc atg      1680
Pro Pro His Val Leu His Arg Lys Lys Leu Gly Phe Pro Val Pro Met
545                 550                 555                 560 cgc cac tgg ctt gcc ggc gat gag ctg ttc ggt tgg gcg cag gac acc      1728
Arg His Trp Leu Ala Gly Asp Glu Leu Phe Gly Trp Ala Gln Asp Thr
                565                 570                 575 atc aag gaa tcc ggt act gaa gat atc ttc aac aag cag gct gtg ctg      1776
Ile Lys Glu Ser Gly Thr Glu Asp Ile Phe Asn Lys Gln Ala Val Leu
            580                 585                 590 gat atg ctg aac gag cac cgc gat ggc gtg tca gat cat tcc cgt cga      1824
Asp Met Leu Asn Glu His Arg Asp Gly Val Ser Asp His Ser Arg Arg
        595                 600                 605 ctg tgg act gtt ctg tca ttt atg gtg tgg cac ggc att ttt gtg gaa      1872
Leu Trp Thr Val Leu Ser Phe Met Val Trp His Gly Ile Phe Val Glu
    610                 615                 620 aac cgc att gat cca cag att gag gac cgc tcc tac cca gtc gag ctt      1920
Asn Arg Ile Asp Pro Gln Ile Glu Asp Arg Ser Tyr Pro Val Glu Leu
625                 630                 635                 640 taa                                                                   1923

<210> SEQ ID NO 38
<211> LENGTH: 2188
<212> TYPE: DNA
<213> ORGANISM: Corynebacterium glutamicum ATCC13032
<220> FEATURE:
<221> NAME/KEY: CDS
<222> LOCATION: (263)..(2182)

<400> SEQUENCE: 38 cccacccctta ccccctacgt tcctacaagg tgcatgtatt aggaaatcaa tctggttttc      60
aggaaccttt gagaatgctg caatagtcag ctgacgcacg ttgcttgagg gagctttcgt     120
caattttggc gtgccctttt cacctcagat gtaacttcgc cgtatcgttg acacgagatt     180
taacaaatgc agcgtcttat ttcttccaac aaaattcctt tgcgatttaa ggcgcctttt     240
atttcaggag gatttttcaa tc atg tgc ggc ctt ctt ggc ata ttg act gca     292
                         Met Cys Gly Leu Leu Gly Ile Leu Thr Ala
                          1               5                  10 aat ggg aac gct gaa gca ttc gtt cct gca ctc gag cgg gcc ttg cca      340
Asn Gly Asn Ala Glu Ala Phe Val Pro Ala Leu Glu Arg Ala Leu Pro
             15                  20                  25 tgc atg cgc cac cgt ggt cct gac gat gcc ggc act tgg cat gac gcc      388
Cys Met Arg His Arg Gly Pro Asp Asp Ala Gly Thr Trp His Asp Ala
         30                  35                  40 gat gca gcg ttt gga ttc aac cgc ctc tcc atc att gat att gca cac      436
Asp Ala Ala Phe Gly Phe Asn Arg Leu Ser Ile Ile Asp Ile Ala His
     45                  50                  55 tcc cac caa cca ctg cgt tgg gga cct gcg gat gaa ccc gac cgc tac      484
Ser His Gln Pro Leu Arg Trp Gly Pro Ala Asp Glu Pro Asp Arg Tyr
 60                  65                  70 gca atg act ttc aac ggt gag atc tac aac tac gtt gag ctg cgt aaa      532
Ala Met Thr Phe Asn Gly Glu Ile Tyr Asn Tyr Val Glu Leu Arg Lys
75                  80                  85                  90 gag ctc tcg gat ttg gga tat gcc ttt aat act tct ggc gat ggc gag      580
Glu Leu Ser Asp Leu Gly Tyr Ala Phe Asn Thr Ser Gly Asp Gly Glu
                 95                 100                 105 cca att gtt gtc ggt ttc cac cac tgg ggc gag tcc gtg gtc gag cat      628
Pro Ile Val Val Gly Phe His His Trp Gly Glu Ser Val Val Glu His
            110                 115                 120
```

|  |  |
|---|---:|
| ctc cgc gga atg ttc ggc att gcc att tgg gat aca aag gaa aag tcg<br>Leu Arg Gly Met Phe Gly Ile Ala Ile Trp Asp Thr Lys Glu Lys Ser<br>125                         130                     135 | 676 |
| ctt ttc ctt gcg cgt gat cag ttc ggc att aag cca ctg ttc tac gca<br>Leu Phe Leu Ala Arg Asp Gln Phe Gly Ile Lys Pro Leu Phe Tyr Ala<br>140                         145                     150 | 724 |
| acc acc gag cat ggc acc gtg ttc tcc tca gag aag aag acc atc ttg<br>Thr Thr Glu His Gly Thr Val Phe Ser Ser Glu Lys Lys Thr Ile Leu<br>155                         160                    165                 170 | 772 |
| gag atg gcc gag gag atg aat cta gat ctg ggc ctt gat aag cgc acc<br>Glu Met Ala Glu Glu Met Asn Leu Asp Leu Gly Leu Asp Lys Arg Thr<br>                       175                    180                    185 | 820 |
| att gag cac tac gtg gac ttg cag tac gtg ccc gag cca gat acc ctt<br>Ile Glu His Tyr Val Asp Leu Gln Tyr Val Pro Glu Pro Asp Thr Leu<br>                     190                       195                   200 | 868 |
| cac gcg cag att tcc cgc ttg gag tca ggc tgc acc gca aca gtt cgt<br>His Ala Gln Ile Ser Arg Leu Glu Ser Gly Cys Thr Ala Thr Val Arg<br>         205                    210                    215 | 916 |
| ccg ggc ggc aag ctg gaa cag aag cgt tac ttc aag cct cag ttc cca<br>Pro Gly Gly Lys Leu Glu Gln Lys Arg Tyr Phe Lys Pro Gln Phe Pro<br>220                         225                    230 | 964 |
| gta cag aag gtc gta aag ggt aag gag cag gac ctc ttc gat cgc att<br>Val Gln Lys Val Val Lys Gly Lys Glu Gln Asp Leu Phe Asp Arg Ile<br>235                         240                    245                 250 | 1012 |
| gcc cag gtg ttg gag gat agc gtc gaa aag cat atg cgt gcc gac gtg<br>Ala Gln Val Leu Glu Asp Ser Val Glu Lys His Met Arg Ala Asp Val<br>                     255                    260                    265 | 1060 |
| acc gta ggc tcg ttc ctt tcc ggc ggt att gac tca acc gca att gcg<br>Thr Val Gly Ser Phe Leu Ser Gly Gly Ile Asp Ser Thr Ala Ile Ala<br>                         270                    275                   280 | 1108 |
| gcg ctt gca aag cgc cac aac cct gac ctg ctc acc ttc acc acc ggt<br>Ala Leu Ala Lys Arg His Asn Pro Asp Leu Leu Thr Phe Thr Thr Gly<br>         285                    290                    295 | 1156 |
| ttc gag cgt gaa ggc tac tcg gag gtc gat gtg gct gcg gag tcc gcc<br>Phe Glu Arg Glu Gly Tyr Ser Glu Val Asp Val Ala Ala Glu Ser Ala<br>300                         305                    310 | 1204 |
| gct gcg att ggc gct gag cac atc gtg aag att gtc tcg cct gag gaa<br>Ala Ala Ile Gly Ala Glu His Ile Val Lys Ile Val Ser Pro Glu Glu<br>315                         320                    325                 330 | 1252 |
| tac gcc aac gcg att cct aag atc atg tgg tac ttg gat gat cct gta<br>Tyr Ala Asn Ala Ile Pro Lys Ile Met Trp Tyr Leu Asp Asp Pro Val<br>                     335                       340                   345 | 1300 |
| gct gac cca tca ttg gtc ccg ctg tac ttc gtg gca gcg gaa gca cgt<br>Ala Asp Pro Ser Leu Val Pro Leu Tyr Phe Val Ala Ala Glu Ala Arg<br>               350                    355                    360 | 1348 |
| aag cac gtc aag gtt gtg ctg tct ggc gag ggc gca gat gag ctg ttc<br>Lys His Val Lys Val Val Leu Ser Gly Glu Gly Ala Asp Glu Leu Phe<br>         365                    370                    375 | 1396 |
| ggt gga tac acc att tac aag gag ccg cta tcg ctt gct cca ttt gag<br>Gly Gly Tyr Thr Ile Tyr Lys Glu Pro Leu Ser Leu Ala Pro Phe Glu<br>380                         385                    390 | 1444 |
| aag atc cct tcc cca cta cgt aaa ggc ctg gga aag ctc agc aag gtt<br>Lys Ile Pro Ser Pro Leu Arg Lys Gly Leu Gly Lys Leu Ser Lys Val<br>395                         400                    405                 410 | 1492 |
| ctg cca gac ggc atg aag ggc aag tcc ctt ctt gag cgt ggc tcc atg<br>Leu Pro Asp Gly Met Lys Gly Lys Ser Leu Leu Glu Arg Gly Ser Met<br>                     415                    420                    425 | 1540 |
| acc atg gaa gag cgc tac tac ggc aac gct cgc tcc ttc aat ttc gag<br>Thr Met Glu Glu Arg Tyr Tyr Gly Asn Ala Arg Ser Phe Asn Phe Glu<br>                     430                      435                   440 | 1588 |

```
cag atg caa cgc gtt att cca tgg gca aag cgc gaa tgg gac cac cgc    1636
Gln Met Gln Arg Val Ile Pro Trp Ala Lys Arg Glu Trp Asp His Arg
        445                 450                 455 gaa gtc act gcg ccg atc tac gca cag tcc cgc aac ttt gat cca gta    1684
Glu Val Thr Ala Pro Ile Tyr Ala Gln Ser Arg Asn Phe Asp Pro Val
460                 465                 470 gcc cgc atg caa cac ctg gat ctg ttc acc tgg atg cgc ggc gac atc    1732
Ala Arg Met Gln His Leu Asp Leu Phe Thr Trp Met Arg Gly Asp Ile
475                 480                 485                 490 ctg gtc aag gct gac aag atc aac atg gcg aac tcc ctt gag ctg cga    1780
Leu Val Lys Ala Asp Lys Ile Asn Met Ala Asn Ser Leu Glu Leu Arg
                495                 500                 505 gtt cca ttc ttg gat aag gaa gtt ttc aag gtt gca gag acc att cct    1828
Val Pro Phe Leu Asp Lys Glu Val Phe Lys Val Ala Glu Thr Ile Pro
        510                 515                 520 tac gac ctg aag att gcc aac ggt acc acc aag tac gcg ctg cgc agg    1876
Tyr Asp Leu Lys Ile Ala Asn Gly Thr Thr Lys Tyr Ala Leu Arg Arg
            525                 530                 535 gca ctc gag cag att gtt ccg cct cac gtt ttg cac cgc aag aag ctg    1924
Ala Leu Glu Gln Ile Val Pro Pro His Val Leu His Arg Lys Lys Leu
540                 545                 550 ggc ttc cct gtt ccc atg cgc cac tgg ctt gcc ggc gat gag ctg ttc    1972
Gly Phe Pro Val Pro Met Arg His Trp Leu Ala Gly Asp Glu Leu Phe
555                 560                 565                 570 ggt tgg gcg cag gac acc atc aag gaa tcc ggt act gaa gat atc ttc    2020
Gly Trp Ala Gln Asp Thr Ile Lys Glu Ser Gly Thr Glu Asp Ile Phe
                575                 580                 585 aac aag cag gct gtg ctg gat atg ctg aac gag cac cgc gat ggc gtg    2068
Asn Lys Gln Ala Val Leu Asp Met Leu Asn Glu His Arg Asp Gly Val
        590                 595                 600 tca gat cat tcc cgt cga ctg tgg act gtt ctg tca ttt atg gtg tgg    2116
Ser Asp His Ser Arg Arg Leu Trp Thr Val Leu Ser Phe Met Val Trp
            605                 610                 615 cac ggc att ttt gtg gaa aac cgc att gat cca cag att gag gac cgc    2164
His Gly Ile Phe Val Glu Asn Arg Ile Asp Pro Gln Ile Glu Asp Arg
620                 625                 630 tcc tac cca gtc gag ctt taagtc                                    2188
Ser Tyr Pro Val Glu Leu
635                 640

<210> SEQ ID NO 39
<211> LENGTH: 29
<212> TYPE: DNA
<213> ORGANISM: Artificial Sequence
<220> FEATURE:
<223> OTHER INFORMATION: Synthetic DNA

<400> SEQUENCE: 39
tttggatccc ccacccttac cccctacgt                                      29

<210> SEQ ID NO 40
<211> LENGTH: 21
<212> TYPE: DNA
<213> ORGANISM: Artificial Sequence
<220> FEATURE:
<223> OTHER INFORMATION: Synthetic DNA

<400> SEQUENCE: 40
gtagatctca tcgttgaaag t                                              21
```

```
<210> SEQ ID NO 41
<211> LENGTH: 21
<212> TYPE: DNA
<213> ORGANISM: Artificial Sequence
<220> FEATURE:
<223> OTHER INFORMATION: Synthetic DNA

<400> SEQUENCE: 41
actttcaacg atgagatcta c                                        21

<210> SEQ ID NO 42
<211> LENGTH: 29
<212> TYPE: DNA
<213> ORGANISM: Artificial Sequence
<220> FEATURE:
<223> OTHER INFORMATION: Synthetic DNA

<400> SEQUENCE: 42
tttggatccg aggtcctgct ccttaccct                                29
```

METHOD FOR PRODUCTION OF L-GLUTAMINE

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 91,390 bytes ASCII (Text) file named "704517SequenceListing.txt," created Feb. 26, 2009.

TECHNICAL FIELD

The present invention relates to a microorganism belonging to the genus *Corynebacterium*, and having the ability to produce and accumulate L-glutamine, and a method of producing L-glutamine using the microorganism.

BACKGROUND ART

It is known that the gluABCD operon of *Corynebacterium glutamicum* encodes a group of proteins of the L-glutamic acid uptake system (non-patent document 1). Although it is known that by disrupting the gluABCD on the chromosome of a microorganism belonging to the genus *Brevibacterium*, the amount of L-glutamic acid produced is increased (patent document 1), it is not known that the amount of L-glutamine produced is increased.

It is known that strains of *Corynebacterium glutamicum* from which each of the three ORFs close to each other on the chromosome thereof, i.e., Ncg12653, Ncg12654, and Ncg12655, is separately deleted, are unable to grow on an agar medium with L-glutamine as the only carbon source, but that each strain retains 80% of the L-glutamine uptake capability of the wild strain, and that the strain lacking Ncg12655, compared with the wild type strain, has an L-glutamic acid content in the cell body thereof increased 2 folds, but has only a slightly increased L-glutamine content (non-patent document 2).

[patent document 1] JP-A-2000-270872
[non-patent document 1] J. Bacteriol., 177, 1152-1158 (1995)
[non-patent document 2] J. Biol. Chem., 281, 12300-12307 (2006)

DISCLOSURE OF THE INVENTION

Problems to be Solved by the Invention

It is an object of the present invention to provide a microorganism having the ability to produce and accumulate L-glutamine, and a process for producing L-glutamine using the microorganism.

Means of Solving the Problems

The present relates to [1] to [4] below.
[1] A microorganism belonging to the genus *Corynebacterium*, wherein the activity of (1) a protein having the amino acid sequence shown by any one of SEQ ID NO:1 to 3, or (2) a protein having a homology of 80% or more to the amino acid sequence shown by any one of SEQ ID NO:1 to 3, and having substantially the same activity as the activity of a protein having the amino acid sequence shown by any one of SEQ ID NO:1 to 3, has been reduced or lost, and wherein the activity of (3) a protein having the amino acid sequence shown by SEQ ID NO:4, or (4) a protein having a homology of 80% or more to the amino acid sequence shown by SEQ ID NO:4, and having substantially the same activity as the activity of a protein having the amino acid sequence shown by SEQ ID NO:4, has been reduced or lost.
[2] The microorganism described in [1], wherein the microorganism belonging to the genus *Corynebacterium* is *Corynebacterium glutamicum*.
[3] A process for producing L-glutamine, comprising culturing the microorganism described in [1] or a microorganism belonging to the genus *Corynebacterium* wherein the activity of one or more proteins selected from (1) to (5) below has been reduced or lost, in a medium to produce and accumulate L-glutamine in the culture, and recovering L-glutamine from the culture:
(1) a protein having the amino acid sequence shown by SEQ ID NO:1,
(2) a protein having the amino acid sequence shown by SEQ ID NO:2,
(3) a protein for having the amino acid sequence shown by SEQ ID NO:3,
(4) a protein having the amino acid sequence shown by SEQ ID NO: 4,
(5) a protein having a homology of 80% or more to the amino acid sequence shown by any one of SEQ ID NO:1 to 4, and having substantially the same activity as the activity of any one of the proteins (1) to (4).
[4] The process for producing L-glutamine described in [3], wherein the microorganism belonging to the genus *Corynebacterium* is *Corynebacterium glutamicum*.

Effect of the Invention

According to the present invention, a microorganism belonging to the genus *Corynebacterium*, and having the ability to efficiently produce and accumulate L-glutamine, can be obtained, and L-glutamine can be produced efficiently using the microorganism.

BEST MODE FOR CARRYING OUT THE INVENTION

1. Preparation of Microorganisms of the Present Invention and Microorganisms Used in the Process of the Present Invention Microorganisms of the present invention and microorganisms used in the process of the present invention include a microorganism wherein the activity of the protein described in (1) or (2) below has been reduced or lost:
(1) a protein having the amino acid sequence shown by any one of SEQ ID NO:1 to 3,
(2) a protein having a homology of 80% or more, preferably 90%, more preferably 95%, still more preferably 98%, and most preferably 99%, to the amino acid sequence shown by any one of SEQ ID NO:1 to 3, and having substantially the same activity as the activity of a protein having the amino acid sequence shown by any one of SEQ ID NO:1 to 3, and wherein the activity of the protein described in (3) or (4) below has been reduced or lost:
(3) a protein having the amino acid sequence shown by SEQ ID NO:4,
(4) a protein having a homology of 80% or more, preferably 90%, more preferably 95%, still more preferably 98%, and most preferably 99%, to the amino acid sequence shown by SEQ ID NO:4, and having substantially the same activity as the activity of a protein having the amino acid sequence shown by SEQ ID NO:4, and a microorganism wherein the activity of one or more proteins selected from among (5) to (9) below has been reduced or lost:

(5) a protein having the amino acid sequence shown by SEQ ID NO:1,
(6) a protein having the amino acid sequence shown by SEQ ID NO:2,
(7) a protein having the amino acid sequence shown by SEQ ID NO:3,
(8) a protein having the amino acid sequence shown by SEQ ID NO:4,
(9) a protein having a homology of 80% or more, preferably 90%, more preferably 95%, still more preferably 98%, and most preferably 99%, to the amino acid sequence shown by any one of SEQ ID NO:1 to 4, and having substantially the same activity as the activity of a protein having the amino acid sequence shown by any one of SEQ ID NO:1 to 4.

Amino acid sequence and nucleotide sequence homologies can be determined using the algorithm BLAST of Karlin and Altschul [Pro. Natl. Acad. Sci. USA, 90, 5873 (1993)] or FASTA [Methods Enzymol., 183, 63 (1990)]. Based on this algorithm BLAST, programs called BLASTN and BLASTX have been developed [J. Mol. Biol., 215, 403 (1990)]. When nucleotide sequences are analyzed with BLASTN on the basis of BLAST, parameters are set to, for example, score=100 and wordlength=12. When amino acid sequences are analyzed with BLASTX on the basis of BLAST, parameters are set to, for example, score=50 and wordlength=3. When the BLAST and Gapped BLAST programs are used, the default parameters of the respective programs are used. The specific ways of these analytical methods are publicly known (http://www.ncbi.nlm.nih.gov.).

A microorganism belonging to the genus *Corynebacterium*, and expressing a protein having a homology of 80% or more to the amino acid sequence shown by any one of SEQ ID NO:1 to 3, and having substantially the same activity as the activity of a protein having the amino acid sequence shown by any one of SEQ ID NO:1 to 3, a protein having a homology of 80% or more to the amino acid sequence shown by SEQ ID NO:4, and having substantially the same activity as the activity of a protein having the amino acid sequence shown by SEQ ID NO:4, or a protein having a homology of 80% or more to the amino acid sequence shown by any one of SEQ ID NO:1 to 4, and having substantially the same activity as the activity of a protein having the amino acid sequence shown by any one of SEQ ID NO:1 to 4, described above, can be identified by the method described below.

That is, by searching a publicly known DNA database or analyzing a chromosomal DNA of a microorganism belonging to the genus *Corynebacterium* by Southern hybridization, a PCR method or the like, to identify a microorganism that expresses a protein having a homology of 80% or more to the amino acid sequence shown by any one of SEQ ID NO:1 to 4, thereafter obtaining a microorganism belonging to the genus *Corynebacterium* wherein the activity of the protein has been lost, in accordance with the method described in J. Bacteriol., 177, 1152-1158 (1995) or J. Biol. Chem., 281, 12300-12307 (2006), and confirming that the microorganism obtained has the same characteristics as those of the microorganism wherein the activity of a protein having the amino acid sequence shown by any one of SEQ ID NO:1 to 4 has been lost, described in the foregoing documents, the microorganism obtained can be identified as the above-described microorganism.

Microorganisms of the present invention and microorganisms used in the process of the present invention can be obtained by a method wherein a mutated type gene that encodes a protein having the amino acid sequence shown by any one of SEQ ID NO:1 to 4, possessed by an existing microorganism wherein the activity of the protein has been reduced or lost, is integrated into one microorganism by transduction using a phage [J. H. Miller, Experiments in Molecular Genetics, Cold Spring Harbor Lab. (1972)], a method Wherein a microorganism is subjected to a mutagenic treatment by UV irradiation, a mutagen and the like, and thereafter a strain wherein the activity of the above-described protein has been reduced or lost is selected, a method wherein protein expression is suppressed, such as the antisense method, or a method wherein a base deletion, substitution or addition is introduced into the nucleotide sequence of a gene that encodes the above-described protein on a chromosomal DNA of a microorganism, and the like.

The region into which a base deletion, substitution or addition is to be introduced is not limited, as far as the activity of the protein described above can be reduced or lost; a transcription regulatory region such as the ORF of the gene that encodes the above-described protein and a promoter of the gene, and a translation regulatory region such as the Shine-Dalgarno sequence can be mentioned; preferably, the ORF of the gene that encodes the above-described protein can be mentioned.

As a transcription regulatory region, a DNA consisting of 50 bases upstream of the 5' terminus of the transcription region on the chromosomal DNA can be mentioned, preferably a region corresponding to the −10 and −35 region can be mentioned.

As a translation regulatory region, a DNA consisting of 30 bases upstream of the 5' terminus of the translation region on the chromosomal DNA can be mentioned, preferably, a DNA consisting of 10 bases on the upstream side can be mentioned.

Introduction of a base deletion, substitution or addition into ORF is not subject to limitations with respect to the choice and number of bases, as far as the base deletion, substitution or addition reduces or loses protein activity; as a base deletion, a deletion of preferably 10 bases or more, more preferably 20 bases or more, still more preferably 100 bases or more, and particularly preferably 200 bases or more, of a portion of the transcription region, and most preferably of the entire transcription region, can be mentioned. As a base substitution, a substitution of a base within the 150th base, preferably within the 100th base, more preferably within the 50th base, particularly preferably within the 30th base, and most preferably within the 20th base, from the 5' terminus of the transcription region, to introduce a nonsense codon, can be mentioned. As a base addition, addition of 50 bases or more, preferably 100 bases or more, more preferably 200 bases or more, still more preferably 500 bases or more, and particularly preferably 1-kb or more, of a DNA fragment just after a base within the 150th base, preferably within the 100th base, more preferably within the 50th base, particularly preferably within the 30th base, and most preferably within the 20th base, from the 5' terminus of the transcription region, can be mentioned; particularly preferably an insertion of a drug resistance gene such as the chloramphenicol resistance gene or the kanamycin resistance gene can be mentioned.

"Protein activity has been reduced" refers to a reduction to 80% or less, preferably 50% or less, more preferably 30% or less, and still more preferably 10% or less, of (1) the amount of the transcription product (mRNA) of the DNA that encodes the protein, quantified by Northern analysis or RT-PCR, and compared with the amount of the mRNA of a gene not incorporating the mutation, or (2) the amount of the protein produced by the microorganism, quantified by SDS-PAGE or an assay using an antibody, and compared with the amount produced of the protein encoded by a gene not incorporating the mutation.

"The activity of any one of proteins having the amino acid sequences shown by SEQ ID NO:1 to 3 has been reduced" refers to a reduction to 80% or less, preferably 50% or less, more preferably 30% or less, and still more preferably 10% or less, of the colony diameter of the microorganism after a given time of culturing by the method described in J. Biol. Chem. 281, 12300-12307 (2006) with L-glutamine as the only carbon source on agar medium, compared with the wild type strain; "the activity of a protein having the amino acid sequence shown by SEQ ID NO:4 has been reduced" refers to a reduction to 80% or less, preferably 50% or less, more preferably 30% or less, and still more preferably 10% or less, of the L-glutamic acid intake activity of the microorganism, compared with the wild type strain by the method described in J. Bacteriol. 177, 1152-1158 (1995).

As a method of introducing a base deletion, substitution or addition into a gene of the chromosomal DNA of a microorganism, a method based on homologous recombination can be mentioned. As a method based on general homologous recombination, a method using a plasmid for homologous recombination that can be prepared by ligating a mutated gene incorporating a base deletion, substitution or addition and a plasmid DNA having a drug resistance gene, which plasmid is incapable of self-replication in the host cell into which a base deletion or the like is to be introduced, can be mentioned.

As a method of obtaining a mutated gene incorporating a base deletion, substitution or addition, a method wherein a desired gene is amplified by a PCR with the chromosomal DNA of the microorganism into which the mutation is to be introduced as the template, and with a synthetic DNA incorporating a previously introduced mutation such as a base deletion, substitution or addition as the primer, to obtain a gene incorporating a base deletion, substitution or addition; a method wherein two regions that sandwich a region to be deleted are amplified by a PCR with the chromosomal DNA of the microorganism into which the mutation is to be introduced as the template, and the amplified fragments obtained are joined to obtain a gene fragment lacking a base, and the like can be mentioned.

As a method based on homologous recombination, a method can be mentioned, the method wherein i) the plasmid for homologous recombination is introduced into a microbial cell by a conventional method, after which a transformant strain having the plasmid for homologous recombination incorporated on the chromosomal DNA by homologous recombination is selected with drug resistance as an index, ii) the transformed strain obtained is cultured in a medium that does not contain the drug for several hours to 1 day, after which the culture is applied to an agar medium containing the drug and an agar medium not containing the drug, and iii) a strain that does not grow in the former medium, but is capable of growing in the latter medium, is selected, whereby a strain undergoing second homologous recombination on the chromosomal DNA is obtained. By determining the nucleotide sequence of the region in which the gene incorporating a deletion or the like on the chromosomal DNA is present, introduction of a base deletion, substitution or addition into the desired gene on the chromosomal DNA can be confirmed.

Using a plasmid having a drug resistance gene and the *Bacillus subtilis* levan sucrase gene sacB [Mol. Microbiol., 6, 1195 (1992)] as a plasmid having a drug resistance gene incapable of self-replication in the microbial cell, and with the use of a method of selection based on the fact that levan sucrase produces a substance harmful to the host cell [J. Bacteriol., 174, 5462 (1992)], the above-described strain undergoing second homologous recombination can also be obtained.

As a method of introducing a plasmid for homologous recombination into a microbial cell, any method allowing introduction of DNA into a microbial cell can be used; for example, the electroporation method [Appl. Microbiol. Biotech., 52, 541 (1999)], the protoplast method [J. Bacteriol., 159, 306 (1984)] and the like can be mentioned.

The microbial cell is preferably a microorganism belonging to the genus *Corynebacterium*, and may be a wild strain or a bred strain bred from the wild strain to produce L-glutamine efficiently.

As microorganisms belonging to the genus *Corynebacterium*, *Corynebacterium acetoacidophilum*, *Corynebacterium acetoglutamicum*, *Corynebacteirum callunae*, *Corynebacterium glutamicum*, *Corynebacterium lactofermentum*, *Corynebacterium herculis*, *Corynebacterium lilium*, *Corynebacterium melassecola*, *Corynebacterium thermoaminogenes*, *Corynebacterium efficiens* and the like can be mentioned. Specifically, *Corynebacterium acetoacidophilum* ATCC 13870, *Corynebacterium acetoglutamicum* ATCC 15806, *Corynebacterium callunae* ATCC 15991, *Corynebacterium glutamicum* ATCC 13032, *Corynebacterium glutamicum* ATCC 13060, *Corynebacterium glutamicum* ATCC 13826, *Corynebacterium glutamicum* ATCC 14020, *Corynebacterium glutamicum* ATCC 13869, *Corynebacterium herculis* ATCC 13868, *Corynebacterium lilium* ATCC 15990, *Corynebacterium melassecola* ATCC 17965, *Corynebacterium thermoaminogenes* ATCC 9244, ATCC 9245, ATCC 9246 and ATCC 9277 and the like can be mentioned, preferably *Corynebacterium glutamicum* ATCC 13032, *Corynebacterium glutamicum* ATCC 13060, *Corynebacterium glutamicum* ATCC 13826, *Corynebacterium glutamicum* ATCC 14020, *Corynebacterium glutamicum* ATCC 13869 and the like can be mentioned.

As strains that have been bred, a microorganism wherein at least one of the mechanisms for controlling L-glutamine biosynthesis has been weakened or nulled, a microorganism obtained by selecting a cell strain that is more resistant to L-glutamine analogues than the wild type strain, and the like can be mentioned.

As examples of a microorganism wherein at least one of the mechanisms for controlling L-glutamine biosynthesis has been weakened or nulled, a coryneform bacterium wherein the activity of glutamine synthetase adenyl transferase, which controls glutamine synthetase by adenylation, has been reduced [FEMS Microbiology Letters, 201, 91 (2001), JP-A-2002-300887], a coryneform bacterium wherein the 405th amino acid of glutamine synthetase to undergo adenylation has been substituted [FEMS Microbiology Letters, 201, 91 (2001), JP-A-2003-164297], and a coryneform bacterium wherein the activity of PII protein has been reduced [FEMS Microbiology Letters, 173, 303 (1999), JP-A-2002-300887] can be mentioned. As examples of a microorganism obtained by selecting a cell strain that is more resistant to L-glutamine analogues than the wild type strain, a coryneform bacterium given azaserine resistance [JP-A-SHO-55-148094], a coryneform bacterium given 6-diazo-5-oxo-norleucine resistance [JP-A-HEI-3-232497] and the like are known.

By the method described above, a microorganism belonging to the genus *Corynebacterium* wherein the activity of the above-described protein has been reduced or lost can be prepared.

2. Process for Producing L-Glutamine of the Present Invention

By culturing a microorganism that can be prepared by the method 1 above in a medium to produce and accumulate L-glutamine in a culture, and recovering L-glutamine from the culture, L-glutamine can be produced.

The medium used in the method of production of the present invention may be any of a synthetic medium and a natural medium, as far as it contains nutrients necessary for the growth of a microorganism of the present invention, and for L-glutamine biosynthesis, such as a carbon source, a nitrogen source, and an inorganic salt.

As the carbon source, which may be any carbon source that can be utilized by the microorganism used, saccharides such as glucose, molasses, fructose, sucrose, maltose, and soybean hydrolyzates, alcohols such as ethanol and glycerol, organic acids such as acetic acid, lactic acid and succinic acid and the like can be mentioned.

As the nitrogen source, ammonia, various inorganic or organic ammonium salts such as ammonium chloride, ammonium sulfate, ammonium carbonate, and ammonium acetate, nitrogen compounds such as urea and amines, and nitrogen-containing organic substances such as meat extract, yeast extract, corn steep liquor, peptone, and soybean hydrolyzates, and the like can be used.

As the inorganic salt, potassium monohydrogen phosphate, potassium dihydrogen phosphate, ammonium sulfate, magnesium sulfate, sodium chloride, ferrous sulfate, calcium carbonate and the like can be used.

In addition, micronutrient sources such as biotin, thiamine, nicotinamide, and nicotinic acid can be added as required. These micronutrient sources can be substituted by medium additives such as meat extract, corn steep liquor and casamino acids. Furthermore, a substance required by a microorganism of the present invention for the growth thereof (for example, an amino acid required for an amino acid auxotrophic microorganism) can be added as required.

The culturing is performed under aerobic conditions like shaking culture or deep spinner culture. Culturing temperature is 20 to 50° C., preferably 20 to 42° C., and more preferably 28 to 38° C. The culturing is performed while keeping the pH of the medium in the range of 5 to 11, preferably in the near-neutral range of 6 to 9. Adjustments of the pH of the medium are performed using an inorganic or organic acid, an alkali solution, urea, calcium carbonate, ammonia, a pH buffer solution and the like.

Culturing time is 5 hours to 6 days, preferably 16 hours to 3 days.

The L-glutamine accumulated in the culture can be recovered by an ordinary method of purification. For example, L-glutamine can be recovered, after completion of the culturing, by removing cells and solid matter from the culture by centrifugation and the like, and then performing publicly known methods such as activated charcoal treatment, ion exchange resin treatment, concentration, and crystal fractionation in combination.

Examples of the invention of this application are given below, to which, however, the invention is not limited.

EXAMPLE 1

Construction of Microorganisms of the Present Invention (1) Preparation of Vector pdX for Chromosomal DNA Homologous Recombination First, by the TA cloning method [Molecular cloning, a laboratory manual, Third Edition, Cold Spring Harbor Laboratory Press (2001), hereinafter abbreviated as Molecular Cloning, 3rd edition], a fragment for chromosome recombination was cloned into the plasmid pESB30.

The plasmid pESB30 is a plasmid having a 2.6-kb PstI DNA fragment comprising the *Bacillus subtilis*-derived levan sucrase gene sacB [Mol. Microbiol., 6, 1195 (1992)] ligated with the PstI cleavage site of the vector pHSG299 having the kanamycin resistance gene (manufactured by Takara Bio Inc.) [Gene, 61, 63 (1987)].

The chromosomal DNA of the wild strain ATCC 13032 of *Corynebacterium glutamicum* used was prepared by the method of Saito et al. [Biochim. Biophys. Acta, 72, 619 (1963)].

After pESB30 was cleaved with BamHI, agarose gel electrophoresis was performed, and an about 5.3-kb DNA fragment was recovered from the agarose gel using GENECLEAN Kit (manufactured by BIO 101).

The 5.3-kb DNA fragment was blunted at both ends thereof using DNA Blunting Kit (manufactured by Takara Bio Inc.) according to the attached protocol. The blunted fragment was concentrated by phenol-chloroform extraction and ethanol precipitation, after the reaction using Takara Ex Taq (manufactured by Takara Bio Inc.) and the attached buffer in the presence of dTTP at 70° C. for 2 hours, to prepare pESB30-T, a DNA fragment wherein one thymine base is added to the 3' terminus thereof.

Using the chromosomal DNA of the *Corynebacterium glutamicum* ATCC 13032 strain as the template, and with synthetic DNAs having the nucleotide sequences shown by SEQ ID NO:6 and 7, or synthetic DNAs having the nucleotide sequences shown by SEQ ID NO:8 and 9, as a primer set, and using Pyrobest DNA polymerase (manufactured by Takara Bio Inc.) and the attached buffer, 2 kinds of PCRs were performed separately.

The about 0.7-kb and about 1.0-kb amplification products obtained by the respective PCRs were each purified using Qiaquick PCR Purification Kit (manufactured by Qiagen).

Furthermore, with the two purified products as the templates, and with synthetic DNAs having the nucleotide sequences shown by SEQ ID NO:6 and 9 as primers, and using Pyrobest DNA Polymerase and the attached buffer, a PCR reaction was carried out, whereby an about 1.7-kb DNA fragment lacking the nucleotide numbers 1001 to 2389 from the nucleotide sequence shown by the nucleotide numbers 261 to 3389 of SEQ ID NO:5 was obtained.

The about 1.7-kb DNA fragment obtained was subjected to agarose gel electrophoresis, and thereafter extracted and purified using GENECLEAN Kit.

The purified DNA fragment obtained above was ligated with the pESB30-T fragment using ligation kit ver.1 (manufactured by Takara Bio Inc.).

Using the binding product obtained, and according to a conventional method, *Escherichia coli* DH5α was transformed. The transformant was applied to an LB agar medium containing 20 µg/ml kanamycin, and thereafter cultured at 30° C. overnight.

The transformant that had grown was transferred to an LB liquid medium containing 20 µg/ml kanamycin and cultured at 30° C. overnight, and the plasmid was extracted by the alkali SDS method from the culture broth obtained.

The plasmid was analyzed by the restriction endonuclease cleavage method, confirming that the plasmid has a structure wherein the about 1.7-kb DNA fragment lacking the nucleotide numbers 1001 to 2389 from the nucleotide sequence shown by the nucleotide numbers 261 to 3389 of SEQ ID NO:5 is inserted into pESB30. The plasmid was named pdX.

(2) Preparation of Vector pdH for Chromosomal DNA Homologous Recombination

A plasmid for deleting the region shown by the nucleotide numbers 2391 to 3424 from the nucleotide sequence shown by the nucleotide numbers 1390 to 4424 of SEQ ID NO:5 on the chromosomal DNA of the *Corynebacterium glutamicum* ATCC 13032 strain was prepared in the same manner as (1).

With the chromosomal DNA of the ATCC 13032 strain prepared in (1) as the template, and with synthetic DNAs having the nucleotide sequences shown by SEQ ID NO:10 and 11, or synthetic DNAs having the nucleotide sequences shown by SEQ ID NO:12 and 13, as a primer set, and using Pyrobest DNA polymerase and the attached buffer, 2 kinds of PCRs were performed separately. The about 1.0-kbp amplification products obtained were each purified using Qiaquick PCR Purification Kit.

Furthermore, with the two purified products as the templates, and with synthetic DNAs having the nucleotide sequences shown by SEQ ID NO:10 and 13 as primers, and using Pyrobest DNA Polymerase and the attached buffer, a PCR reaction was carried out, whereby an about 2.0-kbp DNA fragment lacking the region shown by the nucleotide numbers 2391 to 3424 from the nucleotide sequence shown by the nucleotide numbers 1390 to 4424 of SEQ ID NO:5 was obtained.

The about 2.0-kb DNA fragment obtained was subjected to agarose gel electrophoresis, and thereafter extracted and purified using GENECLEAN Kit.

The purified DNA fragment obtained above was ligated with the pESB30-T fragment prepared in (1) using ligation kit ver.1. Using the binding product obtained, and according to a conventional method, *Escherichia coli* DH5α was transformed. The transformant was applied to an LB agar medium containing 20 µg/ml kanamycin, and thereafter cultured at 30° C. overnight.

The transformant that had grown was transferred to an LB liquid medium containing 20 µg/ml kanamycin and cultured at 30° C. overnight, and the plasmid was extracted by the alkali SDS method from the culture broth obtained.

The plasmid was analyzed by the restriction endonuclease cleavage method, confirming that the plasmid has a structure wherein the about 2.0-kbp DNA fragment lacking the region shown by the nucleotide numbers 2391 to 3424 from the nucleotide sequence shown by the nucleotide numbers 1390 to 4424 of SEQ ID NO:5 is inserted into pESB30. The plasmid was named pdH.

(3) Preparation of Vector pdpG for Chromosomal DNA Homologous Recombination

A plasmid for deleting the region shown by the nucleotide numbers 3627 to 5882 from the nucleotide sequence shown by the nucleotide numbers 2977 to 6882 of SEQ ID NO:5 on the chromosomal DNA of the *Corynebacterium glutamicum* ATCC 13032 strain was prepared in the same manner as (1).

With the chromosomal DNA of the ATCC 13032 strain prepared in (1) as the template, and with synthetic DNAs having the nucleotide sequences shown by SEQ ID NO:14 and 15, or synthetic DNAs having the nucleotide sequences shown by SEQ ID NO:16 and 17, as a primer set, and using Pyrobest DNA polymerase and the attached buffer, 2 kinds of PCRs were performed separately. The about 0.7-kb and about 1.0-kb amplification products obtained were each purified using Qiaquick PCR Purification Kit.

Furthermore, with the two purified products as the templates, and with synthetic DNAs having the nucleotide sequences shown by SEQ ID NO:14 and 17 as primers, and using Pyrobest DNA Polymerase and the attached buffer, a PCR reaction was carried out, whereby an about 1.7-kbp DNA fragment lacking the region shown by the nucleotide numbers 3627 to 5882 from the nucleotide sequence shown by the nucleotide numbers 2977 to 6882 of SEQ ID NO:5 was obtained.

The about 1.7-kb DNA fragment obtained was subjected to agarose gel electrophoresis, and thereafter extracted and purified using GENECLEAN Kit.

The purified DNA fragment obtained above was ligated with the pESB30-T fragment prepared in (1) using ligation kit ver.1.

Using the binding product obtained, and according to a conventional method, *Escherichia coli* DH5α was transformed. The transformant was applied to an LB agar medium containing 20 µg/ml kanamycin, after which it was cultured at 30° C. overnight.

The transformant that had grown was transferred to an LB liquid medium containing 20 µg/ml kanamycin and cultured at 30° C. overnight, and the plasmid was extracted by the alkali SDS method from the culture broth obtained.

The plasmid was analyzed by the restriction endonuclease cleavage method, confirming that the plasmid has a structure wherein the about 1.7-kb DNA fragment lacking the region shown by the nucleotide numbers 3627 to 5882 from the nucleotide sequence shown by the nucleotide numbers 2977 to 6882 of SEQ ID NO:5 is inserted into pESB30. The plasmid was named pdpG.

(4) Preparation of Vector pDGAD for Chromosomal DNA Homologous Recombination

A plasmid for deleting the region shown by the nucleotide numbers 1001 to 4489 from the nucleotide sequence shown by SEQ ID NO:18 on the chromosomal DNA of the *Corynebacterium glutamicum* ATCC 13032 strain was prepared in the same manner as (1).

With the chromosomal DNA of the ATCC 13032 strain prepared in (1) as the template, and with synthetic DNAs having the nucleotide sequences shown by SEQ ID NO:19 and 20, or synthetic DNAs having the nucleotide sequences shown by SEQ ID NO:21 and 22, as a primer set, and using Pyrobest DNA polymerase and the attached buffer, 2 kinds of PCRs were performed separately. The amplification products obtained, each being about 1.0 kbp, were purified using Qiaquick PCR Purification Kit.

Furthermore, with the two purified products as the templates, and with synthetic DNAs having the nucleotide sequences shown by SEQ ID NO:19 and 22 as primers, and using Pyrobest DNA Polymerase and the attached buffer, a PCR reaction was carried out, whereby an about 2.0-kbp DNA fragment lacking the nucleotide numbers 1001 to 4489 from the nucleotide sequence shown by SEQ ID NO:18 was obtained.

The about 2.0-kb DNA fragment obtained was subjected to agarose gel electrophoresis, and thereafter extracted and purified using GENECLEAN Kit.

The purified DNA fragment obtained above was ligated with the pESB30-T fragment prepared in (1), using ligation kit ver.1.

Using the ligation product obtained, and according to a conventional method, *Escherichia coli* DH5α was transformed. The transformant was applied to an LB agar medium containing 20 µg/ml kanamycin, and thereafter cultured at 30° C. overnight.

The transformant that had grown was transferred to an LB liquid medium containing 20 µg/ml kanamycin and cultured at 30° C. overnight, and the plasmid was extracted by the alkali SDS method from the culture broth obtained.

The plasmid was analyzed by the restriction endonuclease cleavage method, confirming that the plasmid has a structure wherein the about 2.0-kb DNA fragment lacking the nucleotide numbers 1001 to 4489 from the nucleotide sequence shown by SEQ ID NO:18 is inserted into pESB30. The plasmid was named pDGAD.

(5) Preparation of Vector pDGB for Chromosomal DNA Homologous Recombination

A plasmid for deleting the nucleotide sequence shown by the nucleotide numbers 1847 to 2734 of SEQ ID NO:18 on the chromosomal DNA of the *Corynebacterium glutamicum* GLA2 strain was prepared in the same manner as (1).

With the chromosomal DNA of the ATCC 13032 strain prepared in (1) as the template, and with synthetic DNAs having the nucleotide sequences shown by SEQ ID NO:23 and 24, or synthetic DNAs having the nucleotide sequences shown by SEQ ID NO:25 and 26, as a primer set, and using Pyrobest DNA polymerase and the attached buffer, 2 kinds of PCRs were performed separately. The amplification products obtained, each being about 1.0 kb, were purified using Qiaquick PCR Purification Kit.

Furthermore, with the two purified products as the templates, and with synthetic DNAs having the nucleotide sequences shown by SEQ ID NO:23 and 26 as primers, and using Pyrobest DNA Polymerase and the attached buffer, a PCR reaction was carried out, whereby an about 2.0-kb DNA fragment lacking the nucleotide numbers 1847 to 2734 from the nucleotide sequence shown by SEQ ID NO:18 was obtained.

The about 2.0-kb DNA fragment obtained was subjected to agarose gel electrophoresis, and thereafter extracted and purified using GENECLEAN Kit.

The purified DNA fragment obtained above was ligated with the pESB30-T fragment prepared in (1), using ligation kit ver.1.

Using the ligation product obtained, and according to a conventional method, *Escherichia coli* DH5α was transformed. The transformant was applied to an LB agar medium containing 20 µg/ml kanamycin, after which it was cultured at 30° C. overnight.

The transformant that had grown was transferred to an LB liquid medium containing 20 µg/ml kanamycin and cultured at 30° C. overnight, and the plasmid was extracted by the alkali SDS method from the culture broth obtained.

The plasmid was analyzed by the restriction endonuclease cleavage method, confirming that the plasmid has a structure wherein the about 2.0-kb DNA fragment lacking the nucleotide numbers 1847 to 2734 from the nucleotide sequence shown by the nucleotide numbers 847 to 3735 of SEQ ID NO:18 is inserted into pESB30. The plasmid was named pDGB.

(6) Introduction of Chromosome Deletion Mutation into L-Glutamine Producing Strain GLA2

By using the fact that the plasmid pdX is incapable of self-replication in a coryneform bacterium, and by the method described below, a strain was selected wherein the DNA fragment for recombination in pdX was incorporated into the chromosomal DNA of the L-glutamine producing strain prepared in Experimental Example, i.e., the *Corynebacterium glutamicum* GLA2 strain (how to make GLA2 is described below), by homologous recombination.

Using pdX, and according to the method of Rest et al. [Appl. Microbiol. Biotech., 52, 541 (1999)], the GLA2 strain was transformed by the electroporation method, and the transformant was applied to a BY agar medium [a medium comprising 20 g of bouillon, 5 g of yeast extract (manufactured by Difco), and 18 g of Bactoagar (manufactured by Difco), contained in 1 L of water, adjusted to pH 7.0] containing 25 µg/ml kanamycin, after which it was cultured at 30° C. overnight.

From 1 strain out of the transformants that had grown, a chromosomal DNA was prepared by a method of Saito et al. [Biochim. Biophys. Acta, 72, 619 (1993)], and the structure of the chromosomal DNA obtained was analyzed by Southern hybridization [Molecular Cloning, 3rd edition]; it was confirmed that pdX was incorporated in the chromosome by homologous recombination of the Campbell type.

The transformant (single recombinant) was applied onto an SUC agar medium [a medium comprising 100 g of sucrose, 7 g of meat extract, 10 g of peptone, 3 g of sodium chloride, 5 g of yeast extract (manufactured by Difco), and 18 g of Bactoagar (manufactured by Difco), contained in 1 L of water, adjusted to pH 7.2], after which it was cultured at 30° C. for 1 day to yield a sucrose-resistant strain.

A chromosomal DNA was prepared from the single recombinant that had grown on the SUC agar medium by the method of Saito et al. With the chromosomal DNA obtained as the template, and with synthetic DNAs having the nucleotide sequences shown by SEQ ID NO:6 and 9 as primers, and using Pyrobest DNA polymerase (manufactured by Takara Bio Inc.) and the attached buffer, a PCR was performed. The nucleotide sequence of the PCR amplification fragment obtained was determined by a conventional method, whereby the GLA2X strain was obtained wherein the original DNA was substituted by a DNA fragment lacking the nucleotide numbers 1001 to 2389 from the nucleotide sequence shown by the nucleotide numbers 261 to 3389 of SEQ ID NO:5 on the chromosomal DNA of the GLA2 strain. In the same manner, using pdH, the GLA2H strain was obtained wherein the original DNA was substituted by a DNA fragment lacking the region shown by the nucleotide numbers 2391 to 3424 from the nucleotide numbers 1390 to 4424 of the nucleotide sequence shown by SEQ ID NO:5. Furthermore, in the same manner, using pdpG, the GLA2PG strain was obtained wherein the original DNA was substituted by a DNA fragment lacking the region shown by the nucleotide numbers 3627 to 5882 from the nucleotide sequence shown by the nucleotide numbers 2977 to 6882 of SEQ ID NO:5.

Using the plasmid pDGAD or pDGB, and in the same manner as described above, a chromosome deletion mutation was introduced into *Corynebacterium glutamicum* GLA2. The strain obtained using pDGAD, lacking the nucleotide numbers 1001 to 4489 from the nucleotide sequence shown by SEQ ID NO:18 on the chromosome, was named the GLA2GAD strain; the strain obtained using pDGB, lacking the nucleotide numbers 1847 to 2734, was named the GLA2 GB strain. Likewise, using pDGB, a chromosome deletion mutation was introduced into the GLA2H strain obtained above. The strain obtained, lacking the nucleotide numbers 1001 to 4489 from the nucleotide sequence shown by SEQ ID NO:18 on the chromosome of the GLA2H strain, was named the GLA2HGB strain.

EXAMPLE 2

Production of L-Glutamine Using a Microorganism of the Present Invention

The GLA2X strain, GLA2H strain, GLA2PG strain, GLA2GAD strain, GLA2 GB strain, and GLA2HGB strain obtained in Example 1, and the GLA2 strain, which is the parent strain thereof, were each inoculated to a test tube containing 8 ml of a seed medium [a medium comprising 50 g of glucose, 7 g of meat extract, 10 g of peptone, 3 g of sodium chloride, 5 g of ammonium sulfate, 5 g of urea, 500 mg of magnesium sulfate heptahydrate, 50 mg of iron sulfate heptahydrate, 500 μg of thiamin hydrochloride, and 20 μg of biotin, contained in 1 L of water, adjusted to pH 7.2, then supplemented with 30 g of calcium carbonate], and cultured under the conditions of 30° C. and 220 rpm for 16 hours, to yield a seed culture broth.

3 ml of each of the seed culture broths was inoculated to a 250-ml baffled conical flask containing 30 ml of a main culture medium [a medium comprising 50 g of glucose, 20 g of ammonium sulfate, 0.5 g of potassium dihydrogen phosphate, 0.5 g of dipotassium hydrogen phosphate, 2 g of urea, 0.5 g of magnesium sulfate heptahydrate, 2 mg of iron sulfate heptahydrate, 2.5 mg of manganese sulfate pentahydrate, 1 mg of thiamin hydrochloride, 100 μg of biotin, and 30 g of calcium carbonate, contained in 1 L of water, sterilized and then adjusted to pH 7.0 with sulfuric acid], and cultured under the conditions of 30° C. and 220 rpm for 16 hours.

Cell bodies were removed from the culture broth via centrifugation, and the amount of L-glutamine accumulated in the culture supernatant was quantified by high performance liquid chromatography (HPLC).

The results are shown in Table 1.

TABLE 1

| Strain | L-glutamine (g/L) |
|---|---|
| GLA2 | 6.0 |
| GLA2X | 15.3 |
| GLA2H | 15.8 |
| GLA2PG | 14.7 |
| GLA2GAD | 10.1 |
| GLA2GB | 9.5 |
| GLA2HGB | 17.2 |

As is evident from Table 1, in a microorganism of the present invention and the GLA2X strain, the GLA2H strain, the GLA2PG strain, the GLA2GAD strain, GLA2 GB, and the GLA2HGB strain, which are microorganisms used in the method of the present invention, the L-glutamine production efficiency improved compared with the parent strain GLA2 strain.

Experimental Example

Construction of L-glutamine producing GLA2 strain (1) Preparation of Plasmid pCglnA2 for Gene Substitution A DNA that encodes a polypeptide having an amino acid sequence wherein the 64th glutamic acid from the N terminus of the amino acid sequence shown by SEQ ID NO:27 was substituted by lysine (Glu64Lys) was obtained using a PCR-based method of site-directed mutagenesis [Molecular Cloning, 3rd edition] as described below.

First, with the chromosomal DNA of the *Corynebacterium glutamicum* ATCC 13032 strain prepared in the same manner as Example 1 (1) as the template, and using Pyrobest DNA polymerase, the attached buffer and the primers described below, a PCR was performed. The primers used in the PCR were synthesized on the basis of the nucleotide sequence information on the DNA that encodes *Corynebacterium glutamicum*-derived glutamine synthetase 2 described in EP 1108790 according to a conventional method, whereby a DNA fragment consisting of a nucleotide sequence wherein the region that encodes the glutamic acid, shown by SEQ ID NO:31, was substituted by the codon (aaa) that encodes lysine, in a region consisting of 21 bases comprising the region that encodes the 64th glutamic acid from the N terminus of the amino acid sequence possessed by the glutamine synthetase 2, shown by SEQ ID NO:27 (the region of the 190th to 192nd bases from the 5' terminus of the nucleotide sequence shown by SEQ ID NO:28, gaa) (the nucleotide sequence of the 180th to 200th bases from the 5' of the nucleotide sequence shown by SEQ ID NO:28, and the nucleotide sequence of the 680th to 700th bases from the 5' of the nucleotide sequence shown by SEQ ID NO:29), and a DNA fragment having the nucleotide sequence of 21 bases shown by SEQ ID NO:32, which is a sequence complementary thereto, were obtained.

A DNA fragment having a tag sequence comprising a BamHI recognition sequence added to the nucleotide sequence of the 167 to 186th bases from the 5' terminus of the nucleotide sequence shown by SEQ ID NO:29 was synthesized, and the nucleotide sequence thereof is shown by SEQ ID NO:30.

A DNA fragment having a tag sequence comprising a BamHI recognition sequence added to a sequence complementary to the nucleotide sequence of the 1185th to 1204th bases from the 5' terminus of the nucleotide sequence shown by SEQ ID NO:29 was synthesized, and the nucleotide sequence thereof is shown by SEQ ID NO:33.

With a DNA fragment having the nucleotide sequence shown by SEQ ID NO:30 and a DNA fragment having the nucleotide sequence shown by SEQ ID NO:32, or a DNA fragment having the nucleotide sequence shown by SEQ ID NO:31 and a DNA fragment having the nucleotide sequence shown by SEQ ID NO:33, each as a primer set, and with the chromosomal DNA obtained as the template, and using Pyrobest DNA polymerase and the attached buffer, 2 kinds of PCRs were performed separately.

The about 0.5-kb amplification products obtained by the respective PCRs (a DNA fragment corresponding to the nucleotide sequence of the 167th to 700th bases from the 5' terminus of the nucleotide sequence shown by SEQ ID NO:29, and a DNA fragment corresponding to the 680th to 1204th) were subjected to agarose gel electrophoresis and extracted and purified using GENECLEAN Kit.

Furthermore, with the two purified products as the templates, and using a DNA fragment having the nucleotide sequence shown by SEQ ID NO:30 and a DNA fragment having the nucleotide sequence shown by SEQ ID NO:33 as primers, a PCR was performed separately. By this PCR, an about 1.0-kb DNA fragment was obtained wherein the codon that encodes the 64th glutamic acid from the N terminus of the amino acid sequence shown by the SEQ ID NO:27 (gaa) was substituted by the codon that encodes lysine (aaa). The about 1.0-kb DNA fragment was treated with BamHI, and subjected to agarose gel electrophoresis, and thereafter extracted and purified using GENECLEAN Kit.

The DNA fragment was inserted into plasmid pESB30.

Specifically, pESB30 was cleaved with BamHI and thereafter treated with alkaline phosphatase, and subjected to agarose gel electrophoresis, and the BamHI-treated fragment of pESB30 was extracted and purified using GENECLEAN Kit. This pESB30 fragment and the BamHI-treated about 1.0-kb DNA fragment obtained above were mixed, and a ligase reaction was carried out using ligation kit ver.1.

Using the reaction product obtained, and according to a conventional method [Molecular Cloning, 3rd edition], *Escherichia coli* DH5α (manufactured by Toyobo) was transformed.

The strain was cultured on an LB agar medium [a medium comprising 10 g of Bactotrypton (manufactured by Difco), 5 g of yeast extract (manufactured by Difco), 10 g of sodium chloride, and 16 g of Bactoagar (manufactured by Difco), contained in 1 L of water, adjusted to pH 7.0] containing 20 µg/ml kanamycin, and a transformant strain was selected. The transformant strain was cultured with an LB medium containing 20 µg/ml kanamycin overnight, and the plasmid was extracted by the alkali SDS method from the culture broth obtained.

A restriction enzyme cleavage analysis was performed, confirming that the plasmid is a plasmid having a structure wherein the about 1.0-kb DNA fragment obtained above was inserted into pESB30. This plasmid was named pCglnA2.

(2) Construction of Plasmid pGlnA2 for Gene Expression

A DNA that encodes a polypeptide having an amino acid sequence wherein the 64th glutamic acid from the N terminus of the amino acid sequence shown by SEQ ID NO:27 has been substituted by lysine (Glu64Lys) was obtained in the same manner as (1).

On the chromosomal DNA of the wild type strain ATCC 13032 of *Corynebacterium glutamicum*, a DNA fragment having a tag sequence comprising a BamHI recognition sequence added to a nucleotide sequence (sequence of the 1st to 20th bases from the 5' terminus of the nucleotide sequence shown by SEQ ID NO:29) located upstream of the 5' terminus of the nucleotide sequence that encodes glutamine synthetase 2, and a DNA fragment having a tag sequence comprising a BamHI recognition sequence added to a sequence complementary to a nucleotide sequence (sequence of the 1825th to 1844th bases from the 5' terminus of the nucleotide sequence shown by SEQ ID NO:29) located on the 3' terminus side were synthesized, and the nucleotide sequences thereof are shown by SEQ ID NO:34 and SEQ ID NO:35, respectively.

With a DNA fragment having the nucleotide sequence shown by SEQ ID NO:34 and a DNA fragment having the nucleotide sequence shown by SEQ ID NO:32, or a DNA fragment having the nucleotide sequence shown by SEQ ID NO:31 and a DNA fragment having the nucleotide sequence shown by SEQ ID NO:35, each as a primer set, and with the chromosomal DNA of ATCC 13032 strain as the template, and using Pyrobest DNA polymerase and the attached buffer, 2 kinds of PCRs were performed separately.

The about 0.7-kb amplification product (a DNA fragment corresponding to the nucleotide sequence of the 1st to 700th bases from the 5' terminus of the nucleotide sequence shown by SEQ ID NO:29) and about 1.1-kb amplification product (a DNA fragment corresponding to the nucleotide sequence of the 680th to 1844th bases from the 5' terminus of the nucleotide sequence shown by SEQ ID NO:29) obtained by the respective PCRs were each subjected to agarose gel electrophoresis, and extracted and purified using GENECLEAN Kit.

Furthermore, with the two purified products as the templates, and using the DNA fragment having the nucleotide sequence shown by SEQ ID NO:34 and the DNA fragment having the nucleotide sequence shown by SEQ ID NO:35 as primers, a PCR was performed separately. By this PCR, an about 1.9-kb DNA fragment comprising a promoter sequence located upstream of the 5' terminus of glutamine synthetase 2 and a nucleotide sequence wherein the codon (gaa) that encodes the 64th glutamic acid from the N terminus of the amino acid sequence shown by SEQ ID NO:27 has been substituted by the codon (aaa) that encodes lysine in SEQ ID NO:28, was obtained. This about 1.9-kb DNA fragment was treated with BamHI, and subjected to agarose gel electrophoresis, and thereafter extracted and purified using GENECLEAN Kit.

pCS299P (pamphlet for International Publication No. 00/63388) was cleaved with BamHI, and thereafter treated with alkaline phosphatase, and subjected to agarose gel electrophoresis, and a pCS299P fragment was extracted and purified using GENECLEAN Kit.

The BamHI-treated about 1.9-kb DNA fragment obtained above was cloned into this pCS299P fragment in the same manner as (1).

A restriction enzyme cleavage analysis was performed, confirming that the plasmid has a structure wherein the about 1.9-kb DNA fragment obtained above is inserted into pCS299P. This plasmid was named pGlnA2.

(3) Preparation of Plasmid pCltsA for Gene Substitution

A DNA that encodes a polypeptide having an amino acid sequence wherein the 80th glycine from the N terminus of the amino acid sequence of the polypeptide involved in lysozyme susceptibility shown by SEQ ID NO:36 is substituted by aspartic acid (Gly80Asp), was obtained in the same manner as (1). It is reported that this mutation causes lysozyme susceptibility [BMC Biotechnol., 9, 1 (2001)].

A DNA fragment having a tag sequence comprising a BamHI recognition sequence added to the nucleotide sequence of the 1st to 20th bases from the 5' terminus of the nucleotide sequence shown by SEQ ID NO:38, which shows a region surrounding the DNA that encodes LtsA on the chromosomal DNA of *Corynebacterium glutamicum* ATCC 13032, and a DNA fragment having a tag sequence comprising a BamHI recognition sequence added to a sequence complementary to the nucleotide sequence of the 981st to 1000th bases from the 5' terminus of the nucleotide sequence shown by SEQ ID NO:38, were synthesized, and the nucleotide sequences thereof are shown by SEQ ID NO:39 and SEQ ID NO:42, respectively. In the region that encodes LtsA shown by SEQ ID NO:37, a DNA fragment consisting of the nucleotide sequence shown by SEQ ID NO:41, wherein the codon that encodes the 80th glycine from the N terminus of the amino acid sequence possessed by LtsA shown by SEQ ID NO:36 (the 238 to 240th nucleotide sequence from the 5' terminus of the nucleotide sequence shown by SEQ ID NO:38, ggt) has been substituted by the codon (gat) that encodes aspartic acid in a region consisting of 21 bases comprising the codon that encodes the glycine (nucleotide sequence of the 229th to 249th bases from the 5' terminus of the nucleotide sequence shown by SEQ ID NO:37, and nucleotide sequence of the 491st to 511th bases from the 5' terminus of the nucleotide sequence shown by SEQ ID NO:38), and a DNA fragment being a sequence complementary to the nucleotide sequence, having the nucleotide sequence of 21 bases shown by SEQ ID NO:40, were synthesized according to a conventional method.

Using a DNA fragment having the nucleotide sequence shown by SEQ ID NO:39 and a DNA fragment having the nucleotide sequence shown by SEQ ID NO:40, or a DNA fragment having the nucleotide sequence shown by SEQ ID NO:41 and a DNA fragment having the nucleotide sequence shown by SEQ ID NO:42, each as a primer set, and with the chromosomal DNA of the ATCC 13032 strain as the template, and using Pyrobest DNA polymerase and the attached buffer, 2 kinds of PCRs were performed separately.

The about 0.5-kb amplification products (a DNA fragment corresponding to the nucleotide sequence of the 1st to 511th bases from the 5' terminus of the nucleotide sequence shown by SEQ ID NO:38, and a DNA fragment corresponding to the nucleotide sequence of the 491st to 1000th bases from the 5' terminus of the nucleotide sequence shown by SEQ ID NO:38) obtained by the respective PCRs were each subjected to agarose gel electrophoresis, and extracted and purified using GENECLEAN Kit.

Furthermore, with the two purified products as the templates, and using the DNA fragment having the nucleotide sequence shown by SEQ ID NO:39 and the DNA fragment having the nucleotide sequence shown by SEQ ID NO:42 as primers, a PCR was performed. By this PCR, an about 1.0-kb DNA fragment was obtained wherein the region (ggt) that encodes the 80th glycine from the N terminus of the amino acid sequence possessed by LtsA shown by SEQ ID NO:36 is substituted by the codon (gat) that encodes aspartic acid. This about 1.0-kb DNA fragment was treated with BamHI and cloned into pESB30 in the same manner as (1), and this plasmid was named pCltsA.

(4) Construction of L-Glutamine Producing Strain GLA2

Using the plasmid pCglnA2 prepared in (1) above, a mutation to substitute the 64th glutamic acid from the N terminus of the amino acid sequence shown by SEQ ID NO:27 by lysine (Glu64Lys) was introduced into the gene that encodes glutamine synthetase 2 on the chromosomal DNA of *Corynebacterium glutamicum* ATCC 13032 by the gene substitution method.

Introduction of a mutation into the gene that encodes glutamine synthetase 2 on the chromosomal DNA of ATCC 13032 by the gene substitution method was performed by the two recombination operations described below. First, by using the fact that the plasmid pCglnA2 prepared above is incapable of self-replication in a coryneform bacterium, a strain was selected wherein this plasmid was incorporated into the chromosomal DNA of *Corynebacterium glutamicum* ATCC 13032 by homologous recombination by the method described below.

Specifically, using the plasmid, and according to the method of Rest et al. [Appl. Microbiol. Biotech., 52, 541 (1999)], by the electroporation method, the ATCC 13032 strain was transformed, and kanamycin-resistant strains were selected. When the structure of the chromosome obtained from 1 strain out of the kanamycin-resistant strains selected was analyzed by Southern hybridization (Molecular Cloning, 3rd edition), it was confirmed that the plasmid was incorporated into the chromosome by homologous recombination of the Campbell type. In such strains, the wild type and the mutated type of the glutamine synthetase 2 gene exist in approximation to each other on the chromosome, and a second homologous recombination is likely to occur therebetween.

The transformant strain (single recombinant) was applied onto an SUC agar medium [a medium comprising 100 g of sucrose, 7 g of meat extract, 10 g of peptone, 3 g of sodium chloride, 5 g of yeast extract (manufactured by Difco), and 18 g of Bactoagar (manufactured by Difco), contained in 1 L of water, adjusted to pH 7.2], and cultured at 30° C. for 1 day, and the colonies that had grown were selected. Because strains wherein the sacB gene is present convert sucrose into a suicide substrate, they are incapable of growing on this medium [J. Bacteriol., 174, 5462 (1991)]. In contrast, in strains lacking the sacB gene as a result of second homologous recombination between the wild type and mutated type of the glutamine synthetase 2 gene existing in approximation to each other on the chromosome, no suicide substrate is formed, and they are capable of growing on this medium. In this second homologous recombination, either the wild type gene or a mutated type gene is deleted along with sacB. In strains lacking both the wild type and sacB, gene substitution to the mutated type has occurred.

The chromosomal DNA of the double recombinant thus obtained was prepared by the method of Saito et al.; with the chromosomal DNA as the template, and with a DNA fragment having the nucleotide sequence shown by SEQ ID NO:30 and a DNA fragment having the nucleotide sequence shown by SEQ ID NO:33 as primers, and using Pyrobest DNA polymerase and the attached buffer, a PCR was performed. The nucleotide sequences of these PCR products were determined by a conventional method, whereby whether the glutamine synthetase 2 gene on the chromosomal DNA of the double recombinant is of the wild type or of the mutated type was determined. As a result, the GS2 strain, which is a double recombinant having a mutation to substitute the 64th glutamic acid from the N terminus of the amino acid sequence shown by SEQ ID NO:27 with lysine (Glu64Lys) in the gene that encodes glutamine synthetase 2 on the chromosomal DNA, was obtained.

A mutation to substitute the 80th glycine from the N terminus of the amino acid sequence shown by SEQ ID NO:36 with aspartic acid (Gly80Asp) was further introduced into the LtsA gene on the chromosomal DNA of the GS2 strain, using pCltsA as described above, whereby the GLA2 strain was obtained. Except that the GS2 strain was used as the host, and that pCltsA was used as the plasmid for substitution, the same operation as described above was performed; the chromosomal DNA of the double recombinant obtained was prepared by the method of Saito et al.; with the chromosomal DNA as the template, and with a DNA fragment having the nucleotide sequence shown by SEQ ID NO:39 and a DNA fragment having the nucleotide sequence shown by SEQ ID NO:42 as primers, and using Pyrobest DNA Polymerase and the attached buffer, a PCR was carried out. The nucleotide sequences of these PCR products were determined by a conventional method, whereby whether the LtsA gene on the chromosomal DNA of the double recombinant is of the wild type or of the mutated type was determined. As a result, the GLA2 strain, which is a double recombinant having a mutation to substitute the 80th glycine from the N terminus of the amino acid sequence shown by SEQ ID NO:36 with aspartic acid in the gene that encodes LtsA on the chromosomal DNA (Gly80Asp), was obtained.

SEQUENCE LISTING FREE TEXT

SEQ ID NO:6—explanation of artificial sequence: synthetic DNA
SEQ ID NO:7—explanation of artificial sequence: synthetic DNA
SEQ ID NO:8—explanation of artificial sequence: synthetic DNA
SEQ ID NO:9—explanation of artificial sequence: synthetic DNA
SEQ ID NO:10—explanation of artificial sequence: synthetic DNA
SEQ ID NO:11—explanation of artificial sequence: synthetic DNA
SEQ ID NO:12—explanation of artificial sequence: synthetic DNA
SEQ ID NO:13—explanation of artificial sequence: synthetic DNA
SEQ ID NO:14—explanation of artificial sequence: synthetic DNA
SEQ ID NO:15—explanation of artificial sequence: synthetic DNA
SEQ ID NO:16—explanation of artificial sequence: synthetic DNA
SEQ ID NO:17—explanation of artificial sequence: synthetic DNA
SEQ ID NO:19—explanation of artificial sequence: synthetic DNA SEQ ID NO:20—explanation of artificial sequence: synthetic DNA
SEQ ID NO:21—explanation of artificial sequence: synthetic DNA
SEQ ID NO:22—explanation of artificial sequence: synthetic DNA
SEQ ID NO:23—explanation of artificial sequence: synthetic DNA
SEQ ID NO:24—explanation of artificial sequence: synthetic DNA
SEQ ID NO:25—explanation of artificial sequence: synthetic DNA
SEQ ID NO:26—explanation of artificial sequence: synthetic DNA
SEQ ID NO:30—explanation of artificial sequence: synthetic DNA
SEQ ID NO:31—explanation of artificial sequence: synthetic DNA
SEQ ID NO:32—explanation of artificial sequence: synthetic DNA
SEQ ID NO:33—explanation of artificial sequence: synthetic DNA
SEQ ID NO:34—explanation of artificial sequence: synthetic DNA
SEQ ID NO:35—explanation of artificial sequence: synthetic DNA
SEQ ID NO:39—explanation of artificial sequence: synthetic DNA
SEQ ID NO:40—explanation of artificial sequence: synthetic DNA
SEQ ID NO:41—explanation of artificial sequence: synthetic DNA
SEQ ID NO:42—explanation of artificial sequence: synthetic DNA

INDUSTRIAL APPLICABILITY

According to the present invention, a microorganism belonging to the genus *Corynebacterium*, and having the capability of efficiently producing and accumulating L-glutamine, can be obtained, and L-glutamine can be produced efficiently using the microorganism.

The invention claimed is:

1. A mutant microorganism belonging to the genus *Corynebacterium*, which has been formed by mutating a parental microorganism belonging to the genus *Corynebacterium*,
   wherein the mutant microorganism produces L-glutamine more efficiently than the parental microorganism,
   wherein the parental microorganism exhibits
   (a) the activity of (1) a protein having the amino acid sequence shown by any one of SEQ ID NO: 1 to 3, or (2) a protein having a homology of 95% or more to the amino acid sequence shown by any one of SEQ ID NO: 1 to 3, and having substantially the same activity as the activity of a protein having the amino acid sequence shown by any one of SEQ ID NO: 1 to 3, and
   (b) the activity of (3) a protein having the amino acid sequence shown by SEQ ID NO: 4, or (4) a protein having a homology of 95% or more to the amino acid sequence shown by SEQ ID NO: 4, and having substantially the same activity as the activity of a protein having the amino acid sequence shown by SEQ ID NO: 4,
   wherein a nucleotide deletion, substitution, or addition to the nucleotide sequence of an endogenous gene of the parental microorganism results in the reduction or loss of the protein activity (a), and
   wherein a nucleotide deletion, substitution, or addition to the nucleotide sequence of an endogenous gene of the parental microorganism results in the reduction or loss of the protein activity (b).

2. The microorganism of claim 1, wherein the microorganism belonging to the genus *Corynebacterium* is *Corynebacterium glutamicum*.

3. A process for producing L-glutamine, comprising
   culturing the microorganism of claim 1 or a mutant microorganism belonging to the genus *Corynebacterium* wherein a parental microorganism belonging to the genus *Corynebacterium* has been mutated so that the activity of one or more proteins selected from
   (1) a protein having the amino acid sequence shown by SEQ ID NO: 1,
   (2) a protein having the amino acid sequence shown by SEQ ID NO: 2,
   (3) a protein having the amino acid sequence shown by SEQ ID NO: 3,
   (4) a protein having the amino acid sequence shown by SEQ ID NO: 4, and
   (5) a protein having a homology of 95% or more to the amino acid sequence shown by any one of SEQ ID NO: 1 to 4, and having substantially the same activity as the activity of any one of the proteins (1) to (4),
   has been reduced or lost relative to the activity of the corresponding one or more proteins in the parental microorganism, in a medium to produce and accumulate L-glutamine in the culture, and
   recovering L-glutamine from the culture,
   wherein the reduction or loss of the activity of each of the one or more proteins is effected by a nucleotide deletion, substitution, or addition to the nucleotide sequence of an endogenous gene encoding each of the one or more proteins, and
   wherein the mutant microorganism produces L-glutamine more efficiently than the parental microorganism.

4. The process for producing L-glutamine of claim 3, wherein the microorganism belonging to the genus *Corynebacterium* is *Corynebacterium glutamicum*.

* * * * *